United States Patent
Seio et al.

(10) Patent No.: US 11,384,112 B2
(45) Date of Patent: Jul. 12, 2022

(54) ARTIFICIAL NUCLEOSIDE AND ARTIFICIAL NUCLEOTIDE, AND ARTIFICIAL OLIGONUCLEOTIDE

(71) Applicants: TOKYO INSTITUTE OF TECHNOLOGY, Tokyo (JP); NISSAN CHEMICAL CORPORATION, Tokyo (JP)

(72) Inventors: Kohji Seio, Tokyo (JP); Yoshiaki Masaki, Tokyo (JP); Keishi Yamamoto, Tokyo (JP); Keita Yoshida, Tokyo (JP); Yusuke Iriyama, Funabashi (JP); Hiroyuki Nakajima, Shiraoka (JP); Tatsuro Kanaki, Shiraoka (JP)

(73) Assignees: TOKYO INSTITUTE OF TECHNOLOGY, Tokyo (JP); NISSAN CHEMICAL CORPORATION, Tokyo (JP)

( * ) Notice: Subject to any disclaimer, the term of this patent is extended or adjusted under 35 U.S.C. 154(b) by 803 days.

(21) Appl. No.: 16/077,969

(22) PCT Filed: Feb. 17, 2017

(86) PCT No.: PCT/JP2017/005835
§ 371 (c)(1),
(2) Date: Dec. 14, 2018

(87) PCT Pub. No.: WO2017/142054
PCT Pub. Date: Aug. 24, 2017

(65) Prior Publication Data
US 2021/0188894 A1    Jun. 24, 2021

(30) Foreign Application Priority Data

Feb. 17, 2016 (JP) .............................. JP2016-028109
Oct. 28, 2016 (JP) ................................ 2016-211476

(51) Int. Cl.
C07H 21/02 (2006.01)
C07H 19/067 (2006.01)

(52) U.S. Cl.
CPC .......... C07H 21/02 (2013.01); C07H 19/067 (2013.01)

(58) Field of Classification Search
None
See application file for complete search history.

(56) References Cited

U.S. PATENT DOCUMENTS 5,466,786 A   11/1995  Buhr et al.
5,969,116 A   10/1999  Martin 2010/0016574 A1   1/2010   Sekine et al.
2011/0269821 A1   11/2011  Swayze et al.
2016/0008389 A1   1/2016   Strämberg et al.

FOREIGN PATENT DOCUMENTS

| JP | H05-504552 A | 7/1993 |
|---|---|---|
| JP | H07-002889 A | 1/1995 |
| JP | 2012-506701 A | 3/2012 |
| JP | 5194256 B2 | 5/2013 |
| WO | WO 2014/131892 A1 | 9/2014 |

OTHER PUBLICATIONS

Keller et al., "Synthesis and hybridization properties of oligonucleotides containing 2'-O-modified ribonucleotides," *Nucleic Acids Res.*, 21(19): 4499-4505 (1993).
Prakash et al., "Zwitterionic oligonucleotides with 2'-O-[3-(N,N-dimethylamino)propyl]-RNA modification: synthesis and properties," *Tetrahedron Letters*, 41(25): 4855-4859 (2000).
Prakash, "An Overview of Sugar-Modified Oligonucleotides for Antisense Therapeutics," *Chem. Biodivers.*, 8(9): 1616-1641 (2011).
European Patent Office, Extended European Search Report in European Patent Application No. 17753309.8 (dated Sep. 26, 2019).
Hwang et al., "Transcription Inhibition Using Modified Pentanucleotides," *Bioorg. Med. Chem.*, 11(10): 2321-2328 (2003).
Milton et al., "Synthesis and Stability of a 2'-O-[N-(Aminoethyl)carbamoyl]methyladenosine-Containing Dinucleotide," *Eur. J. Org. Chem.*, 2013(31): 7184-7192 (2013).
Ozaki et al., "Synthesis and Properties of Oligodeoxyribonucleotides Bearing a Polyamino Group at the 2' Position via 2'-O-Carbamoylmethyl and 2'-S-Carbamoylmethyl Groups," *Nucleosides, Nucleotides and Nucleic Acids*, 28(10): 943-952 (2009).
Yamada et al., "Synthesis of 2'-O-[2-(N-Methylcarbamoyl)ethyl]ribonucleosides Using Oxa-Michael Reaction and Chemical and Biological Properties of Oligonucleotide Derivatives Incorporating These Modified Ribonucleosides," *J. Org. Chem.*, 76(9): 3042-3053 (2011).
Japanese Patent Office, International Search Report in International Patent Application No. PCT/JP2017/005835 (dated Apr. 11, 2017).

*Primary Examiner* — Layla D Berry
(74) *Attorney, Agent, or Firm* — Leydig, Voit & Mayer, Ltd.

(57) ABSTRACT

Provided is an artificial nucleoside or artificial nucleotide capable of composing an artificial oligonucleotide having superior nuclease resistance. The artificial nucleoside or artificial nucleotide is a compound represented by formula (I) or a salt thereof (wherein, Bx represents a pyrimidine base or purine base, $R^1$, $R^2$, $R^3$ and $R^4$ represent hydrogen atoms, C1-6 alkyl groups or the like, Y represents $NR^5R^6$ (wherein, $R^5$ and $R^6$, independently of each other, represent a hydrogen atom, C1-6 alkyl group or the like, or $R^5$ and $R^6$, together with a nitrogen atom bound thereto, form a 3- to 11-membered nitrogen-containing non-aromatic heterocyclic group) or an optionally substituted C2-9 aromatic heterocyclic group, $Z^1$ and $Z^2$ represent hydrogen atoms, hydroxyl group-protecting groups, phosphorous-containing groups or the like, and n represents an integer of 1 to 3).

19 Claims, 2 Drawing Sheets
Specification includes a Sequence Listing.

ated States Patent No. US 11,384,112 B2

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
<223> OTHER INFORMATION: 2'-modified nucleotide PyECE

<400> SEQUENCE: 1
tttttttttt ttttttttt                                                    19

<210> SEQ ID NO 2
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
<223> OTHER INFORMATION: 2'-modified nucleotide DMAECE

<400> SEQUENCE: 2
tttttttttt ttttttttt                                                    19

<210> SEQ ID NO 3
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
```

<223> OTHER INFORMATION: 2'-modified nucleotide MorECE

<400> SEQUENCE: 3
tttttttttt tttttttt                                                   19

<210> SEQ ID NO 4
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
<223> OTHER INFORMATION: 2'-modified nucleotide  BimECE

<400> SEQUENCE: 4
tttttttttt tttttttt                                                   19

<210> SEQ ID NO 5
<211> LENGTH: 20
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(1)
<223> OTHER INFORMATION: 2'-O-methyl-5-methylcytidine
<220> FEATURE:
<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (2)..(2)
<223> OTHER INFORMATION: 2'-modified nucleotide PyECE
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-5-methylcytidine
<220> FEATURE:
<221> NAME/KEY: modified_base
<222> LOCATION: (5)..(5)
<223> OTHER INFORMATION: 2'-modified nucleotide PyECE
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(18)
<223> OTHER INFORMATION: 2'-modified nucleotide PyECE
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine

<400> SEQUENCE: 5
ctgctagcct ctggatttga                                                 20

<210> SEQ ID NO 6
<211> LENGTH: 20
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyl-5-methycytidine
<220> FEATURE:
<221> NAME/KEY: modified_base
<222> LOCATION: (2)..(2)
<223> OTHER INFORMATION: 2'-modified nucleotide DMAECE
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-5-methycytidine
<220> FEATURE:
<221> NAME/KEY: modified_base
<222> LOCATION: (5)..(5)
<223> OTHER INFORMATION: 2'-modified nucleotide DMAECE
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(18)
<223> OTHER INFORMATION: 2'-modified nucleotide DMAECE
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine

<400> SEQUENCE: 6
ctgctagcct ctggatttga                                          20

<210> SEQ ID NO 7
<211> LENGTH: 20
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyl-5-methylcytidine
<220> FEATURE:
<221> NAME/KEY: modified_base
<222> LOCATION: (2)..(2)
<223> OTHER INFORMATION: 2'-modified nucleotide MorECE
<220> FEATURE:

```
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-5-methylcytidine
<220> FEATURE:
<221> NAME/KEY: modified_base
<222> LOCATION: (5)..(5)
<223> OTHER INFORMATION: 2'-modified nucleotide MorECE
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(18)
<223> OTHER INFORMATION: 2'-modified nucleotide MorECE
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine

<400> SEQUENCE: 7
ctgctagcct ctggatttga                                            20

<210> SEQ ID NO 8
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
<223> OTHER INFORMATION: 2'-MOE

<400> SEQUENCE: 8
tttttttttt ttttttttt                                             19

<210> SEQ ID NO 9
<211> LENGTH: 19
<212> TYPE: DNA
<213> ORGANISM: Artificial Sequence
<220> FEATURE:
<223> OTHER INFORMATION: Artificially synthesized oligonucleotide
      sequence
<220> FEATURE:
<221> NAME/KEY: modified_base
<222> LOCATION: (16)..(19)
<223> OTHER INFORMATION: 2'-MCE

<400> SEQUENCE: 9
tttttttttt ttttttttt                                             19

<210> SEQ ID NO 10
<211> LENGTH: 20
<212> TYPE: DNA
<213> ORGANISM: Artificial Sequence
<220> FEATURE:
<223> OTHER INFORMATION: Artificialy synthesized oligonucleotide
      sequence
<220> FEATURE:
```

<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyl-5-methylcytidine
<220> FEATURE:
<221> NAME/KEY: modified_base
<222> LOCATION: (2)..(2)
<223> OTHER INFORMATION: 2'-MCE
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-5-methylcytidine
<220> FEATURE:
<221> NAME/KEY: modified_base
<222> LOCATION: (5)..(5)
<223> OTHER INFORMATION: 2'-MCE
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(18)
<223> OTHER INFORMATION: 2'-MCE
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine

<400> SEQUENCE: 10
ctgctagcct ctggatttga                                           20

<210> SEQ ID NO 11
<211> LENGTH: 20
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(20)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyl-5-methylcytidine
<220> FEATURE:
<221> NAME/KEY: modified_base
<222> LOCATION: (2)..(2)
<223> OTHER INFORMATION: tm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: 2'-O-methyl-5-methylcytidine
<220> FEATURE:
<221> NAME/KEY: modified_base
<222> LOCATION: (5)..(5)

<223> OTHER INFORMATION: tm
<220> FEATURE:
<221> NAME/KEY: modified_base
<222> LOCATION: (8)..(9)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(18)
<223> OTHER INFORMATION: tm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: 2'-O-methyladenosine

<400> SEQUENCE: 11
ctgctagcct ctggatttga                                              20

<210> SEQ ID NO 12
<211> LENGTH: 23
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(23)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(12)
<223> OTHER INFORMATION: 2'-modified nucleotide  BimECE
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-modified nucleotide  BimECE
<220> FEATURE:

```
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-modified nucleotide  BimECE
<220> FEATURE:
<221> NAME/KEY: modified_base
<222> LOCATION: (21)..(22)
<223> OTHER INFORMATION: cm
<220> FEATURE:
<221> NAME/KEY: modified_base
<222> LOCATION: (23)..(23)
<223> OTHER INFORMATION: 2'-O-methyladenosine

<400> SEQUENCE: 12
acaaacacca ttgtcacact cca                                            23

<210> SEQ ID NO 13
<211> LENGTH: 23
<212> TYPE: DNA
<213> ORGANISM: Artificial Sequence
<220> FEATURE:
<223> OTHER INFORMATION: Artificialy synthesized oligonucleotide
      sequence
<220> FEATURE:
<221> NAME/KEY: modified_base
<222> LOCATION: (1)..(23)
<223> OTHER INFORMATION: Phosphorothioate bonds between nucleic acids
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (8)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(12)
```

```
<223> OTHER INFORMATION: 2'-MCE
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: 2'-MCE
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: 2'-O-methyladenosine
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: 2'-MCE
<220> FEATURE:
<221> NAME/KEY: modified_base
<222> LOCATION: (21)..(22)
<223> OTHER INFORMATION: cm
<220> FEATURE:
<221> NAME/KEY: modified_base
<222> LOCATION: (23)..(23)
<223> OTHER INFORMATION: 2'-O-methyladenosine

<400> SEQUENCE: 13
acaaacacca ttgtcacact cca                                          23
```

ARTIFICIAL NUCLEOSIDE AND ARTIFICIAL NUCLEOTIDE, AND ARTIFICIAL OLIGONUCLEOTIDE

CROSS-REFERENCE TO RELATED APPLICATIONS

This patent application is the U.S. national phase of International Patent Application No. PCT/JP2017/005835, filed Feb. 17, 2017, which claims the benefit of Japanese Patent Application No. 2016-028109, filed on Feb. 17, 2016, and Japanese Patent Application No. 2016-211476, filed on Oct. 28, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 10,685 bytes ASCII (Text) file named "740234Sequence-Listing.txt," created Aug. 14, 2018.

TECHNICAL FIELD

The present invention relates to an artificial nucleoside, an artificial nucleotide and an artificial oligonucleotide.

BACKGROUND ART

Nucleic acid pharmaceuticals are pharmaceuticals composed of nucleic acids (oligonucleotides) that form a complementary base pair with a target DNA or RNA, and are expected to be used as a novel type of pharmaceutical. Various artificial nucleic acid units (artificial nucleosides or their phosphoric acid adducts in the form of artificial nucleotides) have been developed in which the structure of a naturally-occurring nucleic acids has been altered for use as a nucleic acid unit used in nucleic acid pharmaceuticals. For example, methoxyethylation (MOE) of the oxygen atom at the 2'-position of the sugar moiety of ribonucleotides is known to improve affinity to a target nucleic acid strand and resistance to nuclease (see, for example, Patent Document 1). An oligonucleotide containing this MOE nucleotide has been approved by the U.S. Food and Drug Administration (FDA) for use as a therapeutic drug for homozygous familial hypercholesterolemia (hoFH), and clinical trials are being conducted for use as a therapeutic drug against various types of diseases such as hypertriglyceridemia or transthyretin (TTR) amyloidosis. Moreover, a methylcarbamoylethylated (MCE) nucleotide has been reported as a modified form of the oxygen atom at the T-position of the sugar moiety of ribonucleotides (see, for example, Patent Document 2 and Non-Patent Document 1). Methylcarbamoylethylation has been reported to considerably improve resistance of this oligonucleotide to nuclease. Oligonucleotides containing this MCE nucleotide have been indicated to significantly enhance the effect of exon skipping in a mouse model of Duchenne muscular dystrophy.

PRIOR ART DOCUMENTS

Patent Documents

Patent Document 1: Japanese Unexamined Patent Publication No. H7-2889
Patent Document 2: Japanese Patent No. 5194256

Non-Patent Documents

Non-Patent Document 1: Journal of Organic Chemistry, Vol. 76, p. 3042 (2011)

DISCLOSURE OF THE INVENTION

Problems to be Solved by the Invention

Oligonucleotides containing the previously described MOE nucleotides or MCE nucleotides do not have adequate resistance to degrading enzymes present in the body in the form of nucleases, and have problems in terms of stability when used as pharmaceuticals. Therefore, there has been a desire for a novel artificial nucleic acid that has been modified at the 2'-position of the sugar moiety.

An object of the present invention is to provide an artificial oligonucleotide modified at the 2'-position of the sugar moiety that demonstrates superior nuclease resistance, and an artificial nucleoside and artificial nucleotide capable of composing the same.

Means for Solving the Problems

The inventors of the present invention found that extremely high nuclease resistance can be obtained by introducing an amino group or heterocyclic group to the nitrogen atom of a carbamoyl ethyl group through an alkyl group, thereby leading to completion of the present invention. Namely, the present invention includes the aspects indicated below.

1. A compound represented by the following formula (I):

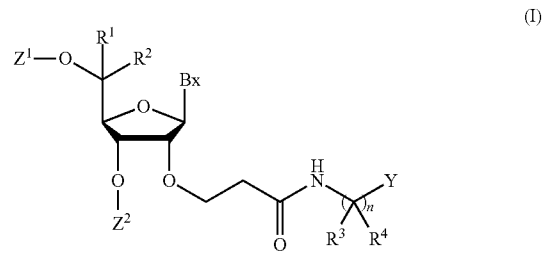

(wherein, Bx represents a purin-9-yl group, 2-oxo-pyrimidin-1-yl group or 2-thioxo-pyrmidin-1-yl group (wherein, the purin-9-yl group, 2-oxo-pyrimidin-1-yl group and 2-thioxo-pyrimidin-1-yl group are, independently of each other, unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group), $Z^1$ and $Z^2$, independently of each other, represent a hydrogen atom, hydroxyl group-protecting group or phosphorous-containing group, $R^1$, $R^2$, $R^3$ and $R^4$, independently of each other, represent a hydrogen atom, halogen atom, cyano group, C1-6 alkyl group or C2-6 alkenyl group (wherein, the C1-6 alkyl group and C2-6 alkenyl group are unsubstituted or substituted with one or more substituents solely or differently selected from the group consisting of a halogen atom, C1-6 alkoxy group and cyano group), Y represents NR⁵R⁶ (wherein, R⁵ and R⁶, independently of each other, represent a hydrogen atom, C1-6 alkyl group, C2-6 alkenyl group (wherein the C1-6 alkyl group and C2-6 alkenyl group are unsubstituted or substituted with one or more substituents solely or differently selected from the group consisting of a halogen atom, cyano group, nitro group, amino group, hydroxyl group, carboxy group, carbamoyl group, C1-6 alkoxy group, C2-6 alkenyloxy group, C1-6 alkoxycarbonyl group, C2-6 alkenyloxycarbonyl group, C1-6 alkylcarbonyl group, C1-6 alkylamino group, C1-6 alkylaminocarbonyl group, C1-6 alkylcarbonyloxy group, C1-6 alkylcarbonylamino group and C1-6 alkoxycarbonylamino group), or C7-10 aralkyl group (wherein, the C7-10 aralkyl group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or R⁵ and R⁶, together with a nitrogen atom bound thereto, form a 3- to 11-membered nitrogen-containing non-aromatic heterocyclic group (wherein, the 3- to 11-membered nitrogen-containing non-aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or C2-9 aromatic heterocyclic group (wherein, the C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), and n represents an integer of 1 to 3; wherein, when n is 2 or 3, two or three $R^3$ and $R^4$ may respectively be the same or different) or a salt thereof.

2. The compound described in 1, wherein Bx represents a 6-aminopurin-9-yl group, 2-amino-6-hydroxypurin-9-yl group, 2-oxo-4-amino-1,2-dihydropyrimidin-1-yl group, 2-oxo-4-amino-5-methyl-1,2-dihydropyrimidin-1-yl group, 2-oxo-4-hydroxy-1,2-dihydropyrimidin-1-yl group or 2-oxo-4-hydroxy-5-methyl-1,2-dihydropyrimidin-1-yl group or the salt thereof.

3. The compound described in 1 or 2, wherein $R^1$, $R^2$, $R^3$ and $R^4$ represent hydrogen atoms, or the salt thereof.

4. The compound described in any of 1 to 3, wherein Y represents NR⁵R⁶, and R⁵ and R⁶, independently of each other, represent a hydrogen atom or C1-3 alkyl group, or the salt thereof.

5. The compound described in any of 1 to 3, wherein Y represents NR⁵R⁶, and R⁵ and R⁶, together with a nitrogen atom bound thereto, form morpholine, or the salt thereof.

6. The compound described in any of 1 to 3, wherein Y represents a pyridyl group, imidazolyl group or benzimidazolyl group, or the salt thereof.

7. The compound described in any of 1 to 6, wherein n is 2, or the salt thereof.

8. The compound described in any of 1 to 7, wherein $Z^1$ is a hydrogen atom or hydroxyl group-protecting group, or the salt thereof.

9. The compound described in any of 1 to 8, wherein $Z^2$ is a hydrogen atom or phosphorous-containing group, or the salt thereof.

10. The compound described in any of 1 to 8, wherein $Z^2$ is a hydroxyl group-protecting group, or the salt thereof.

11. An artificial oligonucleotide containing one or more nucleoside structures represented by the following formula (II):

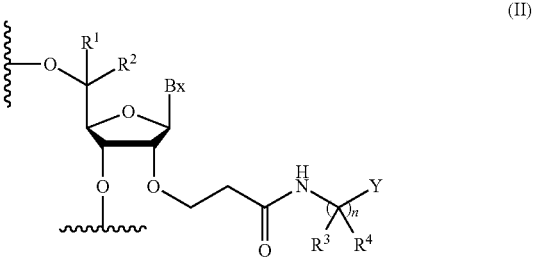

(wherein, Bx represents a purin-9-yl group, 2-oxo-pyrimidin-1-yl group or 2-thioxo-pyrmidin-1-yl group (wherein, the purin-9-yl group, 2-oxo-pyrimidin-1-yl group and 2-thioxo-pyrimidin-1-yl group are, independently of each other, unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group), $R^1$, $R^2$, $R^3$ and $R^4$, independently of each other, represent a hydrogen atom, halogen atom, cyano group, C1-6 alkyl group or C2-6 alkenyl group (wherein, the C1-6 alkyl group and C2-6 alkenyl group are unsubstituted or substituted with one or more substituents solely or differently selected from the group consisting of a halogen atom, C1-6 alkoxy group and cyano group), Y represents NR⁵R⁶ (wherein, R⁵ and R⁶, independently of each other, represent a hydrogen atom, C1-6 alkyl group, C2-6 alkenyl group (wherein the C1-6 alkyl group and C2-6 alkenyl group are unsubstituted or substituted with one or more substituents solely or differently selected from the group consisting of a halogen atom, cyano group, nitro group, amino group, hydroxyl group, carboxy group, carbamoyl group, C1-6 alkoxy group, C2-6 alkenyloxy group, C1-6 alkoxycarbonyl group, C2-6 alkenyloxycarbonyl group, C1-6 alkylcarbonyl group, C1-6 alkylamino group, C1-6 alkylaminocarbonyl group, C1-6 alkylcarbonyloxy group, C1-6 alkylcarbonylamino group and C1-6 alkoxycarbonylamino group), or C7-10 aralkyl group (wherein, the C7-10 aralkyl group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or $R^5$ and $R^6$, together with a nitrogen atom bound thereto, form a 3- to 11-membered nitrogen-containing non-aromatic heterocyclic group (wherein, the 3- to 11-membered nitrogen-containing non-aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or C2-9 aromatic heterocyclic group (wherein, the C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), and n represents an integer of 1 to 3; wherein, when n is 2 or 3, two or three $R^3$ and $R^4$ may respectively be the same or different) or a pharmaceutically acceptable salt thereof.

12. The artificial oligonucleotide described in 11, wherein Bx represents a 6-aminopurin-9-yl group, 2-amino-6-hydroxypurin-9-yl group, 2-oxo-4-amino-1,2-dihydropyrimidin-1-yl group, 2-oxo-4-amino-5-methyl-1,2-dihydropyrimidin-1-yl group, 2-oxo-4-hydroxy-1,2-dihydropyrimidin-1-yl group or 2-oxo-4-hydroxy-5-methyl-1,2-dihydropyrimidin-1-yl group or the pharmaceutically acceptable salt thereof.

13. The artificial oligonucleotide described in 11 or 12, wherein $R^1$, $R^2$, $R^3$ and $R^4$ represent hydrogen atoms, or the pharmaceutically acceptable salt thereof.

14. The artificial oligonucleotide described in any of 11 to 13, wherein Y represents $NR^5R^6$, and $R^5$ and $R^6$, independently of each other, represent a hydrogen atom or C1-3 alkyl group, or the pharmaceutically acceptable salt thereof.

15. The artificial oligonucleotide described in any of 11 to 13, wherein Y represents $NR^5R^6$, and $R^5$ and $R^6$, together with a nitrogen atom bound thereto, form morpholine, or the pharmaceutically acceptable salt thereof.

16. The artificial oligonucleotide described in any of 11 to 13, wherein Y represents a pyridyl group, imidazolyl group or benzimidazolyl group, or the pharmaceutically acceptable salt thereof.

17. The artificial oligonucleotide described in any of 11 to 16, wherein n is 2, or the pharmaceutically acceptable salt thereof.

Effects of the Invention

According to the present invention, an artificial oligonucleotide having superior nuclease resistance, and an artificial nucleoside and artificial nucleotide capable of composing them, are provided.

BEST MODE FOR CARRYING OUT THE INVENTION

Figure 1:
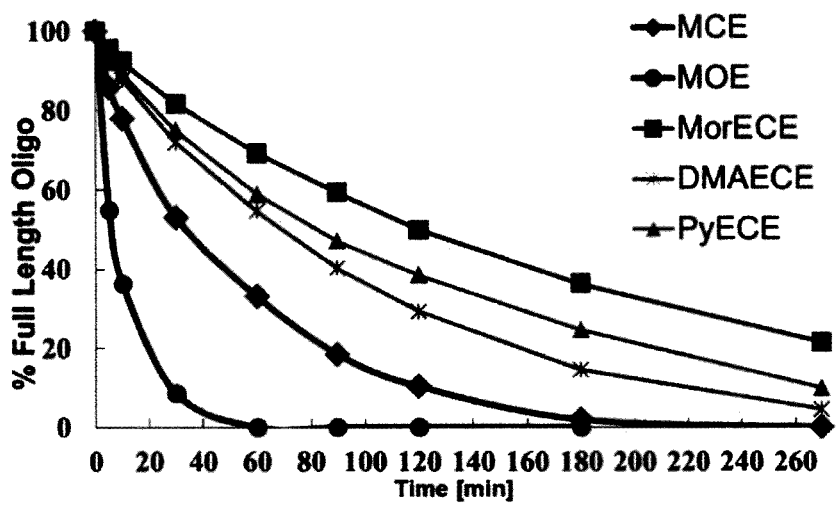
FIG. 1 is a graph indicating exonuclease resistance of artificial oligonucleotides according to the present embodiment.

The terms used in the present description are used with the same meaning as that normally used in the art unless specifically indicated otherwise. The following provides an explanation of each term used in the present description. Furthermore, in the present description, each term has the same meaning whether used individually or used together with other terms unless specifically indicated otherwise.

The term "n-" used in the present description stands for normal, "i-" stands for iso, "sec-" stands for secondary, "tert-" stands for tertiary, "m-" stands for meta, and "p-" stands for para. "Ph" stands for phenyl, "Me" stands for methyl, "Pr" stands for propyl, "Bu" stands for butyl, and "DMTr" stands for dimethoxytrityl.

In addition, in the present description, a "2-oxo-pyrimidin-1-yl group" and "2-thioxo-pyrimidin-1-yl group" are described as omitting the "1H" from a "2-oxo-1H-pyrimidin-1-yl group" and "2-thioxo-1H-pyrimidin-1-yl group", and this applies similarly to a "2-oxo-1,2-dihydropyrimidin-1-yl group" and "2-thioxo-1,2-dihydropyrimidin-1-yl group" as well as "1H-pyrimidin-2-one-1-yl" and "1H-pyrimidin-2-thione-1-yl". Moreover, in the case these partial structures have tautomers, all such tautomers are represented by a single notation.

A substituent protected by a protecting group refers to a functional group in which a hydrogen atom possessed by the functional group is substituted with a protecting group.

A "C2-9 aromatic heterocyclic ring" refers to an aromatic monocyclic or condensed ring having one or more of the same or different heteroatoms, arbitrarily selected from an oxygen atom, sulfur atom and nitrogen atom, in the ring thereof, and having 2 to 9 carbon atoms that compose the ring. Examples of C2-9 aromatic heterocyclic rings include purine, pyrimidine, thiophene, furan, isobenzofuran, pyrrole, imidazole, pyrazole, thiophene, thiazole, isothiazole, isoxazole, oxadiazole, pyridine, pyridazine, pyrazine, indolizine, indole, isoindole, isoquinoline, quinoline, naphthyridine, quinoxaline, quinazoline, pteridine, benzofuran, benzothiophene and benzimidazole.

A "C6-10 aromatic carbon ring" refers to an aromatic monocyclic or condensed ring in which all of the atoms that compose the ring are carbon atoms and the number of atoms that compose the ring is 6 to 10. Examples of C6-10 aromatic carbon rings include benzene and naphthalene.

A "C2-9 aromatic heterocyclic group" refers to a monovalent substituent obtained by removing a single hydrogen atom at an arbitrary location from the aforementioned "C2-9 aromatic heterocyclic ring". Examples of C2-9 aromatic heterocyclic groups include a furyl group, thienyl group, pyridyl group, pyrimidinyl group, pyridazinyl group, pyrazinyl group, pyrrolyl group, imidazolyl group, pyrazolyl group, thiazolyl group, isothiazolyl group, oxazolyl group, isoxazolyl group, oxadiazolyl group (1,2,4-oxadiazolyl group or 1,3,4-oxadiazolyl group), thiadiazolyl group (1,2,4-thiadiazolyl group or 1,3,4-thiadiazolyl group), triazolyl group (1,2,4-triazolyl group or 1,2,3-triazolyl group), tetrazolyl group, triazinyl group, quinolyl group, isoquinolyl group, quinazolyl group, quinoxalyl group, benzofuranyl group, benzothienyl group, benzoxazolyl group, benzisoxazolyl group, benzothiazolyl group, benzisothiazolyl group, benzimidazolyl group, benzotriazolyl group, indolyl group, indazolyl group, pyrrolopyridyl group, pyrazolopyridyl group, imidazopyridyl group, thienopyridyl group, pyrrolopyrazinyl group, pyrazolopyrazinyl group, imidazopyrazinyl group, thienopyrazinyl group, pyrrolopyrimidinyl group, pyrazolopyrimidinyl group, imidazolopyrimidinyl group, thienopyrimidinyl group and pyrazolothienyl group, and preferable examples include a pyridyl group, imidazolyl group and benzimidazolyl group.

A "C6-10 aromatic carbocyclic group" refers to a monovalent substituent obtained by removing a single hydrogen atom at an arbitrary location from the aforementioned "C6-10 aromatic carbon ring". Examples of C6-10 aromatic carbocyclic groups include a phenyl group and naphthyl group.

A "3- to 11-membered nitrogen-containing non-aromatic heterocyclic ring" refers to a non-aromatic heterocyclic ring of a single ring system, condensed ring system (a non-aromatic ring may be condensed into a non-aromatic ring or aromatic ring in the case of the condensed ring system), bridged ring system or spiro ring system in which the number of atoms that compose the ring is 3 to 11. Here, a carbonyl group, thiocarbonyl group, double bond or triple bond may be contained in the ring, and in the case a sulfur atom is included among the atoms that compose the ring, the sulfur atom may be in the form of a sulfinyl group or sulfonyl group. Specific examples of 3- to 11-membered nitrogen-containing non-aromatic heterocyclic rings include azetidin, pyrrolidine, pyrrolidinone, piperidine, piperidinone, azepane, azocane, oxazolidine, isoxazolidine, thiazolidine, isothiazolidine, piperazine, piperazinone, morpholine, thiomorpholine, homomorpholine, homopiperazine, 6,7-dihydro-5H-pyrrolo(3,2-d)pyrimidine, 2,3-dihydro-1H-pyrrolo(2,3-d)pyridazine, 5,6,7,8-tetrahydro-(1,2,4)triazolo(1,5-a)pyrazine, 2,7-diazaspiro[4.4]nonane, 6-oxa-2,9-diazaspiro[4.5]decane, 1,8-diazaspiro[5.5]undecane and 3-azabicyclo[3.3.1]nonane.

A "4- to 8-membered nitrogen-containing non-aromatic heterocyclic ring" refers to the aforementioned "3- to 11-membered nitrogen-containing non-aromatic heterocyclic ring" in which the number of atoms that compose the ring is 4 to 8. Specific examples of 4- to 8-membered nitrogen-containing non-aromatic heterocyclic rings include azetidin, pyrrolidine, pyrrolidinone, piperidine, piperidinone, azepane, azocane, oxazolidine, isoxazolidine, thiazoline, isothiazoline, piperazine, piperazinone, morpholine, thiomorpholine, homomorpholine, homopiperidine and homopiperazine.

A "3- to 11-membered nitrogen-containing non-aromatic heterocyclic group" refers to a monovalent substituent obtained by removing a single hydrogen atom at an arbitrary location from the aforementioned "3- to 11-membered nitrogen-containing non-aromatic heterocyclic ring".

A "4- to 8-membered nitrogen-containing non-aromatic heterocyclic group" refers to a monovalent substituent obtained by removing a single hydrogen atom at an arbitrary location from the aforementioned "4- to 8-membered nitrogen-containing non-aromatic heterocyclic ring".

A "halogen atom" refers to a fluorine atom, chlorine atom, bromine atom or iodine atom.

A "C1-18 alkyl group" refers to a linear or branched saturated hydrocarbon group in which the number of carbon atoms is 1 to 18. Examples of C1-18 alkyl groups include a methyl group, ethyl group, n-propyl group, isopropyl group, n-butyl group, isobutyl group, sec-butyl group, tert-butyl group, n-pentyl group, isopentyl group, neopentyl group, n-hexyl group, n-heptyl group, n-octyl group, n-nonyl group, n-decanyl group, n-undecanyl group, n-dodecanyl group and n-octadecanyl group.

A "C1-6 alkyl group" refers to a linear or branched saturated hydrocarbon group among the aforementioned "C1-18 alkyl groups" in which the number of carbon atoms is 1 to 6. Examples of C1-6 alkyl groups include a methyl group, ethyl group, n-propyl group, isopropyl group, n-butyl group, isobutyl group, sec-butyl group, tert-butyl group, n-pentyl group, isopentyl group, neopentyl group, n-hexyl group and isohexyl group. Similarly, a "C1-4 alkyl group" refers to a linear or branched saturated hydrocarbon group in which the number of carbon atoms is 1 to 4, while a "C1-3 alkyl group" refers to a linear or branched saturated hydrocarbon group in which the number of carbon atoms is 1 to 3.

A "C2-18 alkenyl group" refers to a linear or branched hydrocarbon group, in which the number of carbon atoms is 2 to 18, having one or more double bonds at an arbitrary location. Examples of C2-18 alkenyl groups include a vinyl group, allyl group, propenyl group, isopropenyl group, butenyl group, isobutenyl group, 3-methyl-2-butenyl group, butadienyl group, pentenyl group, isopentenyl group, pentadienyl group, hexenyl group, isohexenyl group, hexadienyl group, heptenyl group, octenyl group, nonenyl group, decanenyl group, undecanenyl group, dodecanenyl group and octadecanenyl group.

A "C2-6 alkenyl group" refers to a linear or branched hydrocarbon group among the aforementioned "C2-18 alkenyl groups", in which the number of carbon atoms is 2 to 6, having one or more double bonds at an arbitrary location. Examples of C2-6 alkenyl groups include a vinyl group, allyl group, propenyl group, isopropenyl group, butenyl group, isobutenyl group, butadienyl group, 3-methyl-2-butenyl group, pentenyl group, isopentenyl group, pentadienyl group, hexenyl group, isohexenyl group and hexadienyl group.

A "C7-10 aralkyl group" refers to a C1-4 alkyl group substituted with a C6-10 aromatic carbocyclic group or C2-9 aromatic heterocyclic group. Examples of C7-10 aralkyl groups include a benzyl group, phenethyl group, 1-phenylethyl group, 3-phenylpropyl group and 4-phenylbutyl group. A "C7-10 aralkyl group" can also be referred to as, for example, a "C2-10 aromatic aralkyl group".

In the case the aforementioned "C7-10 aralkyl group" is substituted with a substituent, the C6-10 aromatic carbocyclic or C2-9 aromatic heterocyclic moiety may be substituted with the substituent, the C1-4 alkyl moiety may be substituted with the substituent, or both may be solely or differently substituted with the substituent, provided there are no particular limitations thereon.

A "C1-6 alkoxy group" refers to a group in which the aforementioned "C1-6 alkyl group" is bound to an oxy group. Examples of C1-6 alkoxy groups include a methoxy group, ethoxy group, n-propoxy group, isopropoxy group, n-butoxy group, tert-butoxy group, isobutoxy group, sec-butoxy group, n-pentyloxy group, isopentyloxy group and n-hexyloxy group.

A "C2-6 alkenyloxy group" refers to a group in which the aforementioned "C2-6 alkenyl group" is bound to an oxy group. Examples of C2-6 alkenyloxy groups include a vinyloxy group, allyloxy group, 1-propenyloxy group, isopropenyloxy group, butenyloxy group, isobutenyloxy group, 3-methyl-2-butenyloxy group, butadienyloxy group, pentenyloxy group, isopentenyloxy group, pentadienyloxy group, hexenyloxy group, isohexenyloxy group and hexadienyloxy group.

A "C1-6 alkoxycarbonyl group" refers to a group in which the aforementioned "C1-6 alkoxy group" is bound to a carbonyl group. Examples of C1-6 alkoxycarbonyl groups include a methoxycarbonyl group, ethoxycarbonyl group, n-propoxycarbonyl group, isopropoxycarbonyl group, n-butoxycarbonyl group, tert-butoxycarbonyl group, isobutoxycarbonyl group, sec-butoxycarbonyl group, pentyloxycarbonyl group, isopentyloxycarbonyl group and n-hexyloxycarbonyl group.

A "C2-6 alkenyloxycarbonyl group" refers to a group in which the aforementioned "C2-6 alkenyloxy group" is bound to a carbonyl group. Examples of C2-6 alkenyloxycarbonyl groups include a vinyloxycarbonyl group, allyloxycarbonyl group, 1-propenyloxycarbonyl group, isopropenyloxycarbonyl group, butenyloxycarbonyl group, isobutenyloxycarbonyl group, 3-methyl-2-butenyloxycarbonyl group, butadienyloxycarbonyl group, pentenyloxycarbonyl group, isopentenyloxycarbonyl group, pentadienyloxycarbonyl group, hexenyloxycarbonyl group, isohexenyloxycarbonyl group and hexadienyloxycarbonyl group.

A "C1-6 alkylcarbonyl group" refers to a group in which the aforementioned "C1-6 alkyl group" is bound to a carbonyl group. Examples of C1-6 alkylcarbonyl groups include an acetyl group, ethylcarbonyl group, n-propylcarbonyl group, isopropylcarbonyl group, n-butylcarbonyl group, tert-butylcarbonyl group, isobutylcarbonyl group, sec-butylcarbonyl group, pentylcarbonyl group, isopentyl carbonyl group and n-hexylcarbonyl group.

A "C1-6 haloalkyl group" refers to a group in which a hydrogen atom at an arbitrary location of the aforementioned "C1-6 alkyl group" is substituted with one or more of the aforementioned "halogen atoms". Examples of C1-6 haloalkyl groups include a monofluormethyl group, monofluoroethyl group, monofluoropropyl group, 2,2,3,3,3-pentafluoropropyl group, monochloromethyl group, trifluoromethyl group, trichloromethyl group, 2,2,2-trifluoroethyl group, 2,2,2-trichloroethyl group, 1,2-dibromoethyl group and 1,1,1-trifluoropropan-2-yl group.

A "C1-6 alkylamino group" includes C1-6 monoalkylamino groups and C1-6 dialkylamino groups. A "C1-6 monoalkylamino group" refers to a group in which one of the aforementioned "C1-6 alkyl groups" is bound to an amino group. Examples of C1-6 monoalkylamino groups included a methylamino group, ethylamino group, n-propylamino group, isopropylamino group, n-butylamino group, n-pentylamino group and n-hexylamino group. A "C1-6 dialkylamino group" refers to a group in which two of the aforementioned "C1-6 alkyl groups" are bound to amino groups. The two amino groups may be the same or different. Examples of C1-6 dialkylamino groups include a dimethylamino group, diethylamino group, N,N-diisopropylamino group, N-methyl-N-ethylamino group, N-isopropyl-N-methylamino group, N-n-butyl-N-methylamino group, N-tert-butyl-N-methylamino group, N-methyl-N-n-pentylamino group, N-n-hexyl-N-methylamino group and N-isopropyl-N-ethylamino group.

A "C1-6 alkylaminocarbonyl group" refers to a group in which the aforementioned "C1-6 alkylamino group" is bound to a carbonyl group.

A "C1-6 alkylcarbonyloxy group" refers to a group in which the aforementioned "C1-6 alkylcarbonyl group is bound to an oxy group.

A "C1-6 alkylcarbonylamino group" refers to a group in which one of the aforementioned "C1-6 alkylcarbonyl groups" is bound to an amino group.

A "C1-6 alkoxycarbonylamino group" refers to a group in which one of the aforementioned "C1-6 alkoxycarbonyl groups" is bound to an amino group.

There are no particular limitations on the "hydroxyl group-protecting group" provided it is a protecting group that is able to stably protect a hydroxyl group during nucleic acid synthesis. More specifically, the hydroxyl group-protecting group is a protecting group that is stable under acidic or neutral conditions and is able to be cleaved by a chemical method in the manner of hydrogenolysis, hydrolysis, electrolysis and photolysis. Examples of hydroxyl group-protecting groups include a C1-6 alkyl group and C2-6 alkenyl group (wherein, the C1-6 alkyl group and C2-6 alkenyl group are unsubstituted or substituted with one or more substituents solely or differently selected from a halogen atom, C1-6 alkoxy group (wherein, the C1-6 alkoxy group is unsubstituted or substituted with one or more substituents solely or differently selected from the following Substituent Group A), C6-10 aromatic carbocyclic group and C2-9 aromatic heterocyclic group (wherein, the C6-10 aromatic carbocyclic group and C2-9 aromatic heterocyclic group are unsubstituted or substituted with one or more substituents solely or differently selected from the following Substituent Group B) and silyl groups, and in the case of being substituted with two or more substituents, the two or more substituents may be mutually bound through single bonds or oxygen atoms), formyl group, aliphatic acyl group, aromatic acyl group, silyl group, tetrahydropyranyl group, tetrahydrothiopyranyl group, tetrahydrofuranyl group, tetrahydrothiofuranyl group, C6-10 aromatic carbocyclic group, C2-9 aromatic heterocyclic group (wherein, the tetrahydropyranyl group, tetrahydrothiopyranyl group, tetrahydrofuranyl group, tetrahydrothiofuranyl group, C6-10 aromatic carbocyclic group, and C2-9 aromatic heterocyclic group are unsubstituted or substituted with one or more substituents solely or differently selected from the following Substituent Group B), C1-6 alkoxycarbonyl group (wherein the C1-6 alkoxycarbonyl group is unsubstituted or substituted with a halogen atom or trialkylsilyl group), C2-6 alkenyloxycarbonyl group, aralkyloxycarbonyl group, (wherein, the aralkyloxycarbonyl group is unsubstituted or the aromatic carbon ring moiety is substituted with one or more substituents solely or differently selected from the following Substituent Group B), aliphatic sulfonyl group, aromatic sulfonyl group, and C1-6 alkylcarbonyl group substituted with a C6-10 aryloxy group.

Here, Substituent Group A is a group of substituents composed of halogen atoms, C1-6 alkoxy groups, C2-6 alkenyloxy groups, cyano group, nitro group, carboxy group, carbamoyl group, amino group, hydroxyl group, C1-6 alkylamino groups, C1-6 alkoxycarbonyl groups, C2-6 alkenyloxycarbonyl groups, C1-6 alkylcarbonyl groups, C1-6 alkylaminocarbonyl groups, C1-6 alkylcarbonyloxy groups, C1-6 alkylcarbonylamino groups, C1-6 alkoxycarbonylamino groups and C6-10 aromatic carbocyclic groups.

Here, Substituent Group B is a group of substituents composed of halogen atoms, C1-6 alkyl groups, C1-6 haloalkyl groups, C1-6 alkoxy groups, C2-6 alkenyl groups, C2-6 alkenyloxy groups, cyano group, nitro group, carboxyl group, carbamoyl group, amino group, hydroxyl group, C1-6 alkylamino groups, C1-6 alkoxycarbonyl groups, C2-6 alkenyloxycarbonyl groups, C1-6 alkylcarbonyl groups, C1-6 alkylaminocarbonyl groups, C1-6 alkylcarbonyloxy groups, C1-6 alkylcarbonylamino groups, C1-6 alkoxycarbonylamino groups and C6-10 aromatic carbocyclic groups.

In addition, C6-10 aryloxy groups refer to groups in which a "C6-10 aromatic carbocyclic group" is bound to an oxy group.

An "aliphatic acyl group" refers to a group in which the aforementioned C1-18 alkyl group or C2-18 alkenyl group (wherein, the C1-18 alkyl group and C2-18 alkenyl group are unsubstituted or substituted with one or more substituents solely or differently selected from the aforementioned Substituent Group A) is bound to a carbonyl group. Examples of aliphatic acyl groups include an acetyl group, propionyl group, butyryl group, isobutyryl group, pentanoyl group, pivaloyl group, valeryl group, isovaleryl group, octanoyl group, nonanoyl group, decanoyl group, 3-methylnonanoyl group, 8-methylnonanoyl group, 3-ethyloctanoyl group, 3,7-dimethyloctanoyl group, undecanoyl group, decanoyl group, tridecanoyl group, tetradecanoyl group, pentadecanoyl group, hexadecanoyl group, 1-methylpentadecanoyl group, 14-methylpentadecanoyl group, 13,13-dimethyltetradecanoyl group, heptadecanoyl group, 15-methylhexadecanoyl group, octadecanoyl group, succinoyl group, glutaroyl group, adipoyl group, chloroacetyl group, dichloroacetyl group, trichloroacetyl group, trifluoroacetyl group, methoxyacetyl group, benzylcarbonyl group and (E)-2-methyl-2-butenoyl group.

An "aromatic acyl group" refers to a monovalent substituent in which a C6-10 aromatic carbocyclic group or C2-9 aromatic heterocyclic group (wherein, the C6-10 aromatic carbocyclic group and C2-9 aromatic heterocyclic group are unsubstituted or substituted with one or more substituents solely or differently selected from the aforementioned Substituent Group B) is bound to a carbonyl group. Examples of aromatic acyl groups include a benzoyl group, α-naphthoyl group, β-naphthoyl group, 2-bromobenzoyl group, 4-chlorobenzoyl group, 2,4,6-trimethylbenzoyl group, 4-toluoyl group, 4-anisoyl group, 2-carboxybenzoyl group, 3-carboxybenzoyl group, 4-carboxybenzoyl group, 4-nitrobenzoyl group, 2-nitrobenzoyl group, 2-(methoxycarbonyl)benzoyl group, 4-phenylbenzoyl group, 2-pyridylcarbonyl group, 4-methoxy-2-pyridylcarbonyl group, 3-pyridylcarbonyl group, 4-pyridylcarbonyl group, 2-pyrimidylcarbonyl group, 4-pyrimidylcarbonyl group, 5-pyrimidylcarbonyl group, 3-pyridazinylcarbonyl group and 4-pyridazinylcarbonyl group.

A "silyl group" refers to a monovalent substituent in which three substituents solely or differently selected from the group consisting of a hydrogen atom, C1-6 alkyl group, C1-6 alkoxy group, C6-10 aromatic carbocyclic group and C2-9 aromatic heterocyclic group are bound to a silicon atom. Examples of silyl groups include a trimethylsilyl group, triethylsilyl group, isopropyldimethylsilyl group, tert-butyldimethylsilyl group, methyldiisopropylsilyl group, methyldi-tert-butylsilyl group, triisopropylsilyl group, diphenylmethylsilyl group, diphenyl-tert-butylsilyl group, diphenylisopropylsilyl group and phenyldiisopropylsilyl group. Here, when a silyl group is bound to an oxygen atom of one hydroxyl group of a molecule having two or more hydroxyl groups, one of the three substituents that compose the silyl group may be substituted with the oxygen atom of a different hydroxyl group of that molecule. In addition, when a silyl group is bound to one hydroxyl group of a molecule having two or more hydroxyl groups and a different silyl group is also bound to an oxygen atom of a different hydroxyl group of that molecule, one of each of the three substituents that compose the two silyl groups may be substituted with a single oxygen atom to form a group represented by the following formula (III).

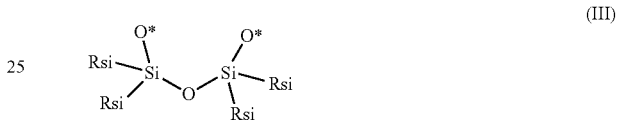

(III)

In the above formula, $R_{Si}$, independently of each other, represents a hydrogen atom, C1-6 alkyl group, C1-6 alkoxy group, C6-10 aromatic carbocyclic group or C2-9 aromatic heterocyclic group, and O* refers to the oxygen atom of the hydroxyl group bound by the silyl group.

Examples of groups represented by the aforementioned formula (III) include groups represented by the following formulas (IV-1) to (IV-4).

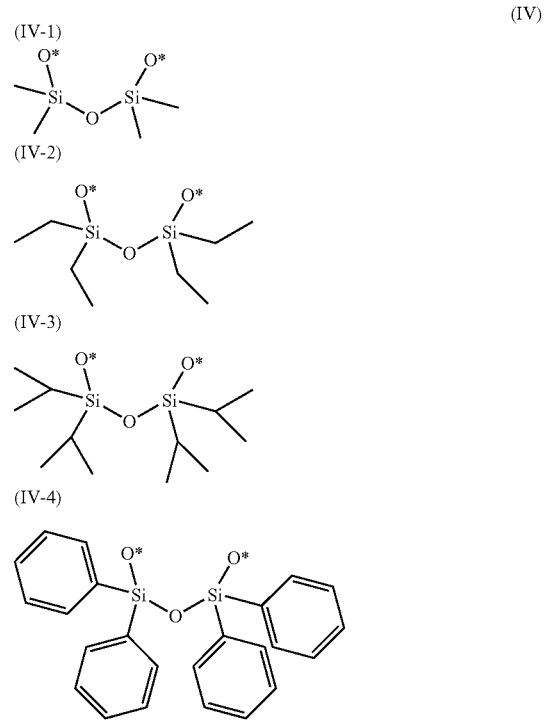

(IV)
(IV-1)
(IV-2)
(IV-3)
(IV-4)

In the formulas, O* refers to the oxygen atom of the hydroxyl group bound by the silyl group.

A "trialkylsilyl group" refers to a monovalent substituent in which three C1-6 alkyl groups are bound to the silicon atom of the aforementioned "silyl group", and examples thereof include a trimethylsilyl group, triethylsilyl group, isopropylsilyl group, tert-butyldimethylsilyl group, methyldiisopropylsilyl group, methyl-di-tert-butylsilyl group and triisopropylsilyl group.

Examples of the "tetrahydropyranyl group" include a tetrahydropyran-2-yl group. Examples of a tetrahydropyranyl group substituted with one or more substituents solely or differently selected from the aforementioned Substituent Group B include a 3-bromotetrahydropyran-2-yl group and 4-methoxytetrahydropyran-4-yl group.

Examples of a "tetrahydrothiopyranyl group" include a tetrahydrothiopyran-2-yl group. Examples of a tetrahydrothiopyranyl group substituted with one or more substituents solely or differently selected from the aforementioned Substituent Group B include a 4-methoxytetrahydrothiopyran-4-yl group.

Examples of a "tetrahydrofuranyl group" include a tetrahydrofuran-2-yl group. Examples of a "tetrahydrothiofuranyl group" include a tetarhydrothiofuran-2-yl group.

An "aliphatic sulfonyl group" refers to a group in which a C1-18 alkyl group or C2-18 alkenyl group (wherein, the C1-18 alkyl group or C2-18 alkenyl group is unsubstituted or substituted with one or more substituents solely or differently selected from the aforementioned Substituent Group A) is bound to a sulfonyl group. Examples of aliphatic sulfonyl groups include a methanesulfonyl group and trifluoromethanesulfonyl group.

An "aromatic sulfonyl group" refers to a monovalent substituent in which a C6-10 aromatic carbocyclic group or C2-9 aromatic heterocyclic group (wherein, the C6-10 aromatic carbocyclic group and C2-9 aromatic heterocyclic group are unsubstituted or substituted with one or more substituents solely or differently selected from the aforementioned Substituent Group B) is bound to a sulfonyl group. Examples of aromatic sulfonyl groups include a benzenesulfonyl group and p-toluenesulfonyl group.

Examples of C1-6 alkyl groups substituted with a C1-6 alkoxy group include a methoxymethyl group, 1,1-dimethyl-1-methoxymethyl group, ethoxymethyl group, n-propoxymethyl group, isopropoxymethyl group, butoxymethyl group, tert-butoxymethyl group, 1-ethoxyethyl group and 1-(isopropoxy)ethyl group.

Examples of C1-6 alkyl groups substituted with a C1-6 alkoxy group substituted with a C1-6 alkoxy group include a 2-methoxyethoxymethyl group.

Examples of C1-6 alkyl groups substituted with a C1-6 alkoxy group substituted with a halogen atom include a 2,2,2-trichloroethoxymethyl group and bis(2-chloroethoxy)methyl group.

Examples of C6-10 aromatic carbocyclic groups substituted with one or more substituents solely or differently selected from the aforementioned Substituent Group B include a 4-chlorophenyl group, 2-fluorophenyl group, 4-methoxyphenyl group, 4-nitrophenyl group and 2,4-dinitrophenyl group.

Examples of C1-6 alkoxycarbonyl groups substituted with a halogen atom or trialkylsilyl group include a 2,2,2-trichloroethoxycarbonyl group and 2-trimethylsilylethoxycarbonyl group.

An aralkyloxycarbonyl group refers to a monovalent substituent in which a C6-10 aromatic carbocyclic group or C2-9 aromatic heterocyclic group is bound to the alkyl moiety of a C1-6 alkoxycarbonyl group. In the case an aralkyloxycarbonyl group is substituted with a substituent, the C6-10 aromatic carbocyclic or C2-9 aromatic heterocyclic moiety may be substituted with the substituent, the C1-6 alkoxycarbonyl moiety may be substituted with the substituent, or both may be solely or differently substituted with the substituent, provided there are no particular limitations thereon.

Examples of aralkyloxycarbonyl groups that are unsubstituted or a C6-10 aromatic carbon ring moiety is substituted with one or more substituents solely or differently selected from the aforementioned Substituent Group B include a benzyloxycarbonyl group, 4-methoxybenzyloxycarbonyl group, 3,4-dimethoxybenzyloxycarbonyl group, 2-nitrobenzyloxycarbonyl group and 4-nitrobenzyloxycarbonyl group.

Preferable examples of hydroxyl group-protecting groups in Bx include C1-6 alkyl groups and C2-6 alkenyl groups (wherein, the C1-6 alkyl group and C2-6 alkenyl group is unsubstituted or substituted with one to three C6-10 aromatic carbocyclic groups (wherein, the C6-10 aromatic carbocyclic group is unsubstituted or substituted with one or more substituents solely or differently selected from the aforementioned Substituent Group B), tetrahydropyranyl groups, aliphatic acyl groups, aromatic acyl groups, silyl groups and C6-10 aromatic carbocyclic groups (wherein, the C6-10 aromatic carbocyclic group is substituted with one or more substituents solely or differently selected from the group consisting of a halogen atom, C1-6 alkoxy group and nitro group). More preferably, examples of hydroxyl group-protecting groups include C1-6 alkyl groups (wherein, the C1-6 alkyl group is unsubstituted or substituted with one to three C6-10 aromatic carbocyclic groups (wherein, the C6-10 aromatic carbocyclic group is unsubstituted or substituted with one or more substituents solely or differently selected from a methoxy group and nitro group)), aliphatic acyl groups, aromatic acyl groups and silyl groups, even more preferably, examples of hydroxyl group-protecting groups include a benzoyl group and benzyl group, and particularly preferably, examples of hydroxyl group-protecting groups include a benzoyl group.

There are no particular limitations on the "sulfanyl group-protecting group" provided it is a protecting group capable of stably protecting a sulfanyl group during nucleic acid synthesis. More specifically, the sulfanyl group-protecting group is a protecting group that is stable under acidic or neutral conditions and is able to be cleaved by a chemical method in the manner of hydrogenolysis, hydrolysis, electrolysis and photolysis.

Examples thereof include groups that form a disulfide bond in addition to the groups previously listed as examples of the aforementioned "hydroxyl group-protecting groups". Examples of groups that form a disulfide bond include alkylthio groups (such as a methylthio group, ethylthio group or tert-butylthio group) and alkylthio groups substituted with a C6-10 aromatic carbocyclic group (such as a benzylthio group).

A preferable sulfanyl group-protecting group is an aliphatic acyl group or aromatic acyl group. The sulfanyl group-protecting group is more preferably a benzoyl group.

There are no particular limitations on the "amino group-protecting group" provided it is capable of stably protecting an amino group during nucleic acid synthesis. More specifically, the amino group-protecting group is a protecting group that is stable under acidic or neutral conditions and is able to be cleaved by a chemical method in the manner of hydrogenolysis, hydrolysis, electrolysis and photolysis.

Examples thereof include groups previously listed as examples of the aforementioned "hydroxyl group-protecting groups".

The amino group-protecting group in Bx is preferably an aliphatic acyl group, aromatic acyl group or C1-6 alkylcarbonyl group substituted with a C6-10 aryloxy group. The amino group-protecting group is more preferably an acetyl group, propionyl group, butyryl group, isobutyryl group, pivaloyl group, benzoyl group, monomethoxybenzoyl group, dimethoxybenzoyl group, trimethoxybenzoyl group or phenoxyacetyl group, even more preferably an acetyl group, isobutyryl group or benzoyl group, and particularly preferably a benzoyl group.

Publications widely known among persons with ordinary skill in the art, such as Protective Groups in Organic Synthesis, fourth edition, T. W. Green, ed., John Wiley & Sons Inc. (2006), can be referred to with respect to the introduction and de-protection of the "hydroxyl group-protecting group", "sulfanyl group-protecting group" and "amino group-protecting group" in the present invention.

[Artificial Nucleoside and Artificial Nucleotide]

The artificial nucleoside and artificial nucleotide of the present embodiment is a compound represented by the following formula (I) or a salt thereof. An oligonucleotide demonstrating extremely superior nuclease resistance can be composed by introducing an amino group or heterocyclic group into a nitrogen atom of a carbamoyl group of an oxygen atom at the 2'-position via an alkyl group.

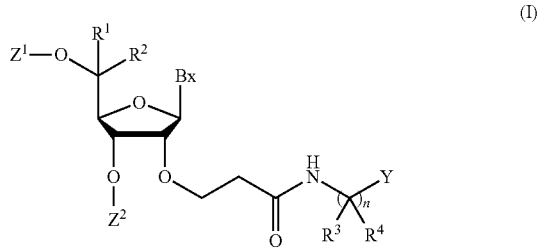

(I)

Bx represents a purin-9-yl group, 2-oxo-pyrimidin-1-yl group or 2-thioxo-pyrmidin-1-yl group, the purin-9-yl group, 2-oxo-pyrimidin-1-yl group and 2-thioxo-pyrimidin-1-yl group are, independently of each other, unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group.

$Z^1$ and $Z^2$, independently of each other, represent a hydrogen atom, hydroxyl group-protecting group or phosphorous-containing group.

$R^1$, $R^2$, $R^3$ and $R^4$, independently of each other, represent a hydrogen atom, halogen atom, cyano group, C1-6 alkyl group or C2-6 alkenyl group, and the C1-6 alkyl group and C2-6 alkenyl group are unsubstituted or substituted with one or more substituents solely or differently selected from the group consisting of a halogen atom, C1-6 alkoxy group and cyano group.

Y represents $NR^5R^6$ or a C2-9 aromatic heterocyclic group. In $NR^5R^6$, $R^5$ and $R^6$, independently of each other, represent a hydrogen atom, C1-6 alkyl group, C2-6 alkenyl group (wherein the C1-6 alkyl group and C2-6 alkenyl group are unsubstituted or substituted with one or more substituents solely or differently selected from the group consisting of a halogen atom, cyano group, nitro group, amino group, hydroxyl group, carboxy group, carbamoyl group, C1-6 alkoxy group, C2-6 alkenyloxy group, C1-6 alkoxycarbonyl group, C2-6 alkenyloxycarbonyl group, C1-6 alkylcarbonyl group, C1-6 alkylamino group, C1-6 alkylaminocarbonyl group, C1-6 alkylcarbonyloxy group, C1-6 alkylcarbonylamino group and C1-6 alkoxycarbonylamino group), C7-10 aralkyl group (wherein, the C7-10 aralkyl group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or $R^5$ and $R^6$, together with a nitrogen atom bound thereto, form a 3- to 11-membered nitrogen-containing non-aromatic heterocyclic group (wherein, the 3- to 11-membered nitrogen-containing non-aromatic heterocyclic group is unsubstituted or is substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group).

The C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group.

n represents an integer of 1 to 3. Here, when n is 2 or 3, two or three $R^3$ and $R^4$ may respectively be the same or different.

Furthermore, the artificial nucleoside of the present embodiment refers to a compound represented by formula (I) in which $Z^1$ and $Z^2$ represent hydrogen atoms, while the artificial nucleotide refers to a compound represented by formula (I) in which at least one of $Z^1$ and $Z^2$ represents a phosphorous-containing group.

Bx represents a purin-9-yl group, 2-oxo-pyrimidin-1-yl group or 2-thioxo-pyrimidin-1-yl group. The purin-9-yl group, 2-oxo-pyrimidin-1-yl group and 2-thioxo-pyrimidin-1-yl group may be unsubstituted or may be substituted with one or more substituents solely or differently selected from the group consisting of a halogen atom, C1-6 alkyl group, amino group, hydroxyl group and sulfanyl group. Here, the amino group may be unsubstituted or may be substituted with an amino group-protecting group. In addition, the hydroxyl group may be unsubstituted or substituted with a hydroxyl group-protecting group. The sulfanyl group may be unsubstituted or substituted with a sulfanyl group-protecting group.

The purin-9-yl group, 2-oxo-pyrimidin-1-yl group and 2-thioxo-pyrimidin-1-yl group refer to substituted or unsubstituted heterocyclic groups that compose a base moiety of an artificial nucleoside or artificial nucleotide and contain a residue of a nucleic acid base or an analogue thereof. Examples of naturally-occurring bases include adenine (A), guanine (G), thymine (T), cytosine (C) and uracil (U). Nucleic acid bases are not limited thereto, but rather include other artificial or naturally-occurring nucleic acid bases. Examples thereof include 5-methylcytosine (5-me-C), 5-hydroxymethylcytosine, xanthine, hypoxanthine, 2-aminoadenine and 2-thiothymine.

Specific examples of Bx include the groups represented by the following formulas (V-1) to (V-10).

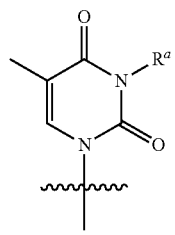
(V-1)

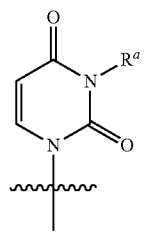
(V-2)

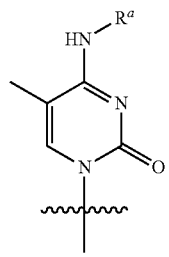
(V-3)

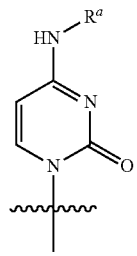
(V-4)

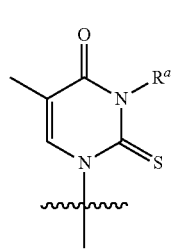
(V-5)

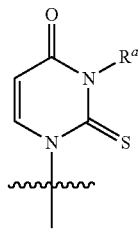
(V-6)

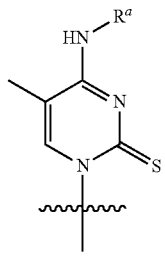
(V-7)

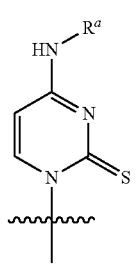
(V-8)

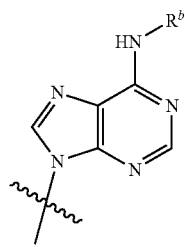
(V-9)

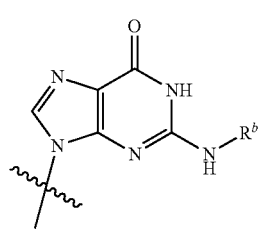
(V-10)

$R^a$ represents a hydrogen atom or amino group-protecting group, and $R^b$ represents a hydrogen atom or amino group-protecting group.

The amino group-protecting group in $R^a$ is preferably a C1-6 alkyl group, aliphatic acyl group, aromatic acyl group or C1-6 alkylcarbonyl group substituted with a C6-10 aryloxy group.

The amino group-protecting group in $R^b$ is preferably a C1-6 alkyl group, aliphatic acyl group, aromatic acyl group or C1-6 alkylcarbonyl group substituted with a C6-10 aryloxy group.

$R^a$ is preferably a hydrogen atom, isobutyryl group, acetyl group, benzoyl group or phenoxyacetyl group, and particularly preferably a hydrogen atom. $R^b$ is preferably a hydrogen atom, isobutyryl group, acetyl group, benzoyl group or phenoxyacetyl group, and particularly preferably a hydrogen atom.

Bx is preferably a purin-9-yl group or 2-oxo-pyrmidin-1-yl group. The purin-9-yl group and 2-oxo-pyrimidin-1-yl group may be unsubstituted or may be substituted with one or more substituents solely or differently selected from the group consisting of a halogen atom, C1-6 alkyl group, amino group, hydroxyl group and sulfanyl group. Here, the amino group may be unsubstituted or substituted with an amino group-protecting group. In addition, the hydroxyl group may be unsubstituted or substituted with a hydroxyl group-protecting group. The sulfanyl group may be unsubstituted or substituted with a sulfanyl group-protecting group.

Bx is more preferably at least one type selected from the group consisting of a 6-aminopurin-9-yl group (adenine residue; $R^b$=H in V-9), 2-amino-6-hydroxypurin-9-yl group (guanine residue; $R^b$=H in V-10), 2-oxo-4-amino-1,2-dihydropyrimidin-1-yl group (cytosine residue; $R^a$=H in V-4), 2-oxo-4-amino-5-methyl-1,2-dihydropyrimidin-1-yl group (5-methylcytosine residue; $R^a$=H in V-3), 2-oxo-4-hydroxy-1,2-dihydropyrimidin-1-yl group (uracil residue; $R^a$ H in V-2) or 2-oxo-4-hydroxy-5-methyl-1,2-dihydropyrimidin-1-yl group (thymine residue; $R^a$=H in V-1), even more preferably a 2-oxo-4-hydroxy-1,2-dihydropyrimidin-1-yl group or 2-oxo-4-hydroxy-5-methyl-1,2-dihydropyrimidin-1-yl group, and particularly preferably a 2-oxo-4-hydroxy-5-methyl-1,2-dihydropyrimidin-1-yl group.

$Z^1$ and $Z^2$, independently of each other, represent a hydrogen atom, hydroxyl group-protecting group or phosphorous-containing group.

Examples of the hydroxyl group-protecting group in $Z^1$ and $Z^2$ include a hydroxyl group-protecting group, which is the previously described "protecting group that is able to stably protect a hydroxyl group during nucleic acid synthesis". Preferable examples include a C1-6 alkyl group, C2-6 alkenyl group, aliphatic acyl group, aromatic acyl group, tetrahydropyranyl group, silyl group, aliphatic sulfonyl group and aromatic sulfonyl group. Here, the C1-6 alkyl group and C2-6 alkenyl group are unsubstituted or substituted with one to three substituents solely or differently selected from the group consisting of a halogen atom, C1-6 alkoxy group (wherein, the C1-6 alkoxy group is unsubstituted or substituted with one or more substituents solely or differently selected from the aforementioned Substituent Group A), C6-10 aromatic carbocyclic group and C2-9 aromatic heterocyclic group (wherein, the C6-10 aromatic carbocyclic group and C2-9 aromatic heterocyclic group are unsubstituted or substituted with one or more substituents solely or differently selected from the aforementioned Substituent Group B). In addition, when $Z^1$ is a silyl group, one of the substituents that compose the silyl group may be substituted for an oxygen atom at the 3'-position, and when $Z^2$ is a silyl group, one of the substituents that compose the silyl group may be substituted for an oxygen atom at the 5'-position. In addition, when $Z^1$ and $Z^2$ are silyl groups, $Z^1$ and $Z^2$ may form a group represented by the following formula (III) together with oxygen atoms respectively bound thereto.

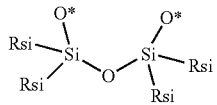
(III)

In the above formula, $R_{Si}$, independently of each other, represents a hydrogen atom, C1-6 alkyl group, C1-6 alkoxy group, C6-10 aromatic carbocyclic group or C2-9 aromatic heterocyclic group, and O* refers to an oxygen atom of a hydroxyl group bound by the silyl group.

The hydroxyl group-protecting group in $Z^1$ and $Z^2$ is more preferably a C1-6 alkyl group, tetrahydropyranyl group, aliphatic acyl group, aromatic acyl group or silyl group. Here, the C1-6 alkyl group is unsubstituted or substituted with one to three substituents solely or differently selected from the group consisting of a halogen atom, C1-6 alkoxy group and C6-10 aromatic carbocyclic group (wherein, the C6-10 aromatic carbocyclic group is unsubstituted or substituted with one or more substituents solely or differently selected from the aforementioned Substituent Group B).

The hydroxyl group-protecting group in $Z^1$ and $Z^2$ is more preferably a C1-6 alkyl group or silyl group.

Here, the C1-6 alkyl group is substituted with one to three substituents solely or differently selected from the group consisting of a C6-10 aromatic carbocyclic group (wherein the C6-10 aromatic carbocyclic group is unsubstituted or substituted with one or more substituents solely or differently selected from the aforementioned Substituent Group B). In addition, $Z^1$ and $Z^2$ may also form a group represented by the aforementioned formula (III) together with oxygen atoms respectively bound thereto.

The phosphorous-containing group in $Z^1$ and $Z^2$ refers to a group that contains a phosphorous atom, and the group that is useful for forming an internucleoside bond contained by a phosphodiester structure or phosphorothioate structure. Phosphorous-containing groups known in the art can be used for the phosphorous-containing group in $Z^1$ and $Z^2$, and examples thereof include groups derived from phosphoramidite, groups derived from H-phosphonate, groups derived from phosphate esters and groups derived from phosphate triesters.

More specifically, examples include groups represented by any of the formulas ($Z^2$-1) to ($Z^3$-3) indicated below.

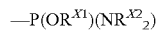
—P(OR$^{X1}$)(NR$^{X2}$₂)            Formula ($Z^2$-1):

In the above formula, $R^{X1}$ and $R^{X2}$, independently of each other, represent a C1-6 alkyl group, and the C1-6 alkyl group is unsubstituted or substituted with one or more substituents solely or differently selected from the group consisting of a halogen atom, C1-6 alkoxy group, cyano group, C6-10 aromatic carbocyclic group and C2-9 aromatic heterocyclic group.

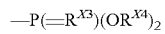
—P(=R$^{X3}$)(OR$^{X4}$)₂            Formula ($Z^2$-2):

In the above formula, $R^{X3}$ represents an oxygen atom or sulfur atom, $R^{X4}$, independently of each other, represent a hydrogen atom, hydroxyl group-protecting group, C1-6 alkyl group or C6-10 aromatic carbocyclic group, the C1-6 alkyl group is unsubstituted or substituted with one or more substituents solely or differently selected from a halogen atom, C1-6 alkoxy group, cyano group, C6-10 aromatic carbocyclic group and C2-9 aromatic heterocyclic group, and the aromatic carbocyclic group is unsubstituted or substituted with one or more substituents solely or differently selected from the group consisting of a halogen atom, C1-6 alkoxy group, C1-6 alkyl group and cyano group.

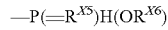
—P(=R$^{X5}$)H(OR$^{X6}$)            Formula ($Z^2$-3):

In the above formula, $R^{X5}$ represents an oxygen atom or sulfur atom and $R^{X6}$ represents a hydrogen atom, hydroxyl group-protecting group or C6-10 aromatic carbocyclic group.

The "hydroxyl group-protecting group" in $R^{X4}$ and $R^{X6}$ is preferably a C1-6 alkyl group, C2-6 alkenyl group, aliphatic acyl group, aromatic acyl group, methyl group substituted with one to three C6-10 aromatic carbocyclic groups, or C6-10 aromatic carbocyclic group, and the C6-10 aromatic carbocyclic groups are substituted with a substituent solely or differently selected from a halogen atom, alkoxy group and nitro group. More preferably, the hydroxyl group-protecting group is a benzoyl group, benzyl group, 2-chlorophenyl group, 4-chlorophenyl group or 2-propenyl group (allyl group).

The phosphorous-containing group is preferably any of the groups represented by formulas ($Z^2$-4) to ($Z^2$-6).

$$—P(OR^{X1})(NR^{X2}_2) \quad \text{Formula } (Z^2\text{-4})$$

In the above formula, $R^{X1}$ represents a C1-6 alkyl group C1-6 alkyl group substituted with a cyano group, and $R^{X2}$ represents a C1-6 alkyl group.

$$—P(=O)(OH)_2 \quad \text{Formula } (Z^2\text{-5}):$$

$$—P(=O)H(OH) \quad \text{Formula } (Z^2\text{-6}):$$

The phosphorous-containing group is more preferably a cyanoethoxy(diisopropylamino)phosphino group (group represented by the formula —P(OC₂H₄CN)(N(i-Pr)₂) or hydroxyphosphinyl group (group represented by the formula —P(=O)H(OH)).

$Z^1$ is preferably a hydrogen atom or hydroxyl group-protecting group. In the case $Z^1$ is a hydroxyl group-protecting group, the hydroxyl group-protecting group is presumed to be used to produce the artificial nucleotide of the present embodiment after being de-protected. Consequently, there are no limitations on the hydroxyl group-protecting group provided it is able to stably protect a hydroxyl group during nucleic acid synthesis, and the type and structure of the protecting group may be the same or different in each artificial nucleotide and artificial nucleoside. $Z^1$ is more preferably a hydrogen atom, acetyl group, tert-butyl group, tert-butoxymethyl group, methoxymethyl group, tetrahydropyranyl group, 1-ethoxyethyl group, 1-(2-chloroethoxy)ethyl group, 2-trimethylsilylethyl group, p-chlorophenyl group, 2,4-dinitrophenyl group, benzyl group, benzoyl group, p-phenylbenzoyl group, 2,6-dichlorobenzyl group, levulinoyl group, diphenylmethyl group, p-nitrobenzyl group, trimethylsilyl group, triethylsilyl group, tert-butyldimethylsilyl group, tert-butyldiphenylsilyl group, triphenylsilyl group, triisopropylsilyl group, benzoyl formate group, chloroacetyl group, trichloroacetyl group, trifluoroacetyl group, pivaloyl group, isobutyryl group, 9-fluorenylmethyloxycarbonyl group, methanesulfonyl group, p-toluenesulfonyl group, trifluoromethanesulfonyl group, triphenylmethyl group (trityl group), monomethoxytrityl group, dimethoxytrityl group (DMTr group), trimethoxytrityl group, 9-phenylxanthen-9-yl group (Pixyl group) or 9-(p-methoxyphenyl)xanthen-9-yl group (MOX group). $Z^1$ is even more preferably a hydrogen atom, benzyl group, triethylsilyl group, tert-butyldimethylsilyl group, tert-butyldiphenylsilyl group, triisopropylsilyl group, trityl group, monomethoxytrityl group, dimethoxytrityl group or trimethoxytrityl group, still more preferably a hydrogen atom, trityl group, monomethoxytrityl group, dimethoxytrityl group or trimethoxytrityl group, and particularly preferably a hydrogen atom or trityl group. $Z^1$ is most preferably a dimethoxytrityl group.

$Z^2$ is preferably a hydrogen atom or phosphorous-containing group, and more preferably a hydrogen atom, group represented by the formula —P(OC₂H₄CN)(N(i-Pr)₂) or group represented by the formula —P(=O)H(OH).

In another aspect thereof, $Z^2$ is preferably a hydroxyl group-protecting group that serves as an intermediate in the process of producing a compound represented by the aforementioned formula (I) or a salt thereof. Consequently, there are no limitations on the hydroxyl group-protecting group provided it is able to stably protect a hydroxyl group during nucleic acid synthesis, and the type and structure of the protecting group may be the same or different in each artificial nucleotide and artificial nucleoside. In the case $Z^2$ is a hydroxyl group-protecting group, the hydroxyl group-protecting group is preferably an acetyl group, tert-butyl group, tert-butoxymethyl group, methoxymethyl group, tetrahydropyranyl group, 1-ethoxyethyl group, 1-(2-chloroethoxy)ethyl group, 2-trimethylsilylethyl group, benzyl group, benzoyl group, p-phenylbenzoyl group, 2,6-dichlorobenzyl group, levulinoyl group, diphenylmethyl group, p-nitrobenzyl group, trimethylsilyl group, triethylsilyl group, tert-butyldimethylsilyl group, tert-butyldiphenylsilyl group, triphenylsilyl group, triisopropylsilyl group, benzoyl formate group, chloroacetyl group, trichloroacetyl group, trifluoroacetyl group, pivaloyl group, isobutyryl group, 9-fluorenylmethyloxycarbonyl group, methanesulfonyl group, p-toluenesulfonyl group or trifluoromethanesulfonyl group. The hydroxyl group-protecting group is more preferably a trimethylsilyl group, triethylsilyl group, tert-butyldimethylsilyl group, tert-butyldiphenylsilyl group, triphenylsilyl group or triisopropylsilyl group.

In another aspect thereof, $Z^1$ and $Z^2$ preferably form a group represented by any of the following formulas (IV-1) to (IV-4) together with an oxygen atom respectively bound by $Z^1$ and $Z^2$, and particularly preferably form a group represented by the following formula (IV-3).

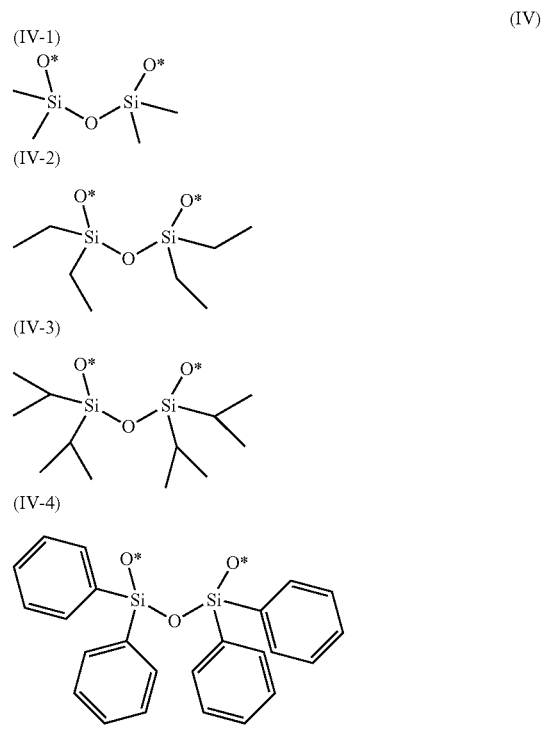

In the above formulas, O* refers to an oxygen atom of a hydroxyl group bound by the silyl group.

$R^1$ and $R^2$, independently of each other, represent a hydrogen atom, halogen atom, cyano group, C1-6 alkyl group or C2-6 alkenyl group. Here, the C1-6 alkyl group and C2-6 alkenyl group are unsubstituted or substituted with one or more substituents solely or differently selected from the group consisting of a halogen atom, C1-6 alkoxy group and cyano group.

$R^1$ is preferably a hydrogen atom or C1-3 alkyl group and more preferably a hydrogen atom. $R^2$ is preferably a hydrogen atom or C1-3 alkyl group and more preferably a hydrogen atom.

$R^3$ and $R^4$, independently of each other, represent a hydrogen atom, halogen atom, cyano group, C1-6 alkyl group or C2-6 alkenyl group. Here, the C1-6 alkyl group and C2-6 alkenyl group are unsubstituted or substituted with one or more substituents solely or differently selected from the group consisting of a halogen atom, C1-6 alkoxy group and cyano group. Here, when n is 2 or 3, $R^3$ may respectively be the same or different and $R^4$ may respectively be the same or different.

$R^3$ is preferably a hydrogen atom or C1-3 alkyl group and more preferably a hydrogen atom. $R^4$ is preferably a hydrogen atom or C1-3 alkyl group and more preferably a hydrogen atom.

When Y is $NR^5R^6$, $R^5$ and $R^6$, independently of each other, represent a hydrogen atom, C1-6 alkyl group, C2-6 alkenyl group or C7-10 aralkyl group. Here, the C1-6 alkyl group and C2-6 alkenyl group are unsubstituted or substituted with one or more substituents solely or differently selected from the group consisting of a halogen atom, cyano group, nitro group, amino group, hydroxyl group, carboxy group, carbamoyl group, C1-6 alkoxy group, C2-6 alkenyloxy group, C1-6 alkoxycarbonyl group, C2-6 alkenyloxycarbonyl group, C1-6 alkylcarbonyl group, C1-6 alkylamino group, C1-6 alkylaminocarbonyl group, C1-6 alkylcarbonyloxy group, C1-6 alkylcarbonylamino group and C1-6 alkoxycarbonylamino group, and the C7-10 aralkyl group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group.

$R^5$ is preferably a hydrogen atom or C1-3 alkyl group and more preferably a methyl group.

$R^6$ is preferably a hydrogen atom or C1-3 alkyl group and more preferably a methyl group.

In another aspect thereof, $R^5$ and $R^6$ may form a 3- to 11-membered nitrogen-containing non-aromatic heterocyclic ring together with a nitrogen atom bound thereto. Here, the 3- to 11-membered nitrogen-containing non-aromatic heterocyclic ring is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group.

The 3- to 11-membered nitrogen-containing non-aromatic heterocyclic ring formed by $R^5$ and $R^6$ together with a nitrogen atom bound thereto is preferably a 4- to 8-membered nitrogen-containing non-aromatic heterocyclic ring containing 4 to 6 methylene groups, and examples thereof include piperidine, pyrrolidine, morpholine, thiomorpholine, homopiperidine and homomorpholine. More preferred are those containing an oxygen atom or sulfur atom for an atom that composes the ring, and examples thereof include morpholine, thiomorpholine and homomorpholine. The 3- to 11-membered nitrogen-containing non-aromatic heterocyclic ring formed by $R^5$ and $R^6$ together with a nitrogen atom bound thereto is particularly preferably morpholine. In addition, the 4- to 8-membered nitrogen-containing non-aromatic heterocyclic ring is preferably unsubstituted.

In another aspect thereof, Y may be a C2-9 aromatic heterocyclic group. Y is preferably a pyridyl group, imidazolyl group or benzimidazolyl group, more preferably a 2-pyridyl group, imidazol-1-yl group or (benzimidazol)-1-yl group, and particularly preferably a 2-pyridyl group or (benzimidazol)-1-yl group.

n represents the number of repeating unit structures, is an integer of 1 to 3 and is preferably 2.

There are cases in which the compound represented by formula (I) has isomers. In that case, the compound of the present embodiment is not limited to a specific isomer, but rather includes all possible isomers (such as keto-enol tautomers, imine-enamine tautomers, diastereomers, optical isomers and rotational isomers), racemic bodies and mixtures thereof.

One or more hydrogen atoms, carbon atoms and/or other atoms in the compound represented by formula (I) can each be substituted with isotopes of hydrogen atoms, carbon atoms and/or other atoms. Examples of such isotopes include $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively, and hydrogen, carbon, nitrogen, oxygen, phosphorous, sulfur, fluorine, iodine and chlorine are included in these isotopes. Compounds represented by formula (I) include compounds substituted with such isotopes. Compounds substituted with these isotopes are also useful as pharmaceuticals and include all radioactively labeled forms of compounds represented by formula (I). In addition, "radioactive labeling methods" for producing these "radioactively labeled forms" are also included in the present invention, and are useful as tools for metabolic pharmacokinetics research, tools for research on binding assays and/or diagnostic tools.

The radioactively labeled form of the compound represented by formula (I) can be prepared by a method commonly known in the art. For example, tritium-labeled form of the compound represented by formula (I) can be prepared by introducing tritium into a specific compound represented by formula (I) by a catalytic dehalogenation reaction using tritium. This method comprises the reaction of tritium gas with a precursor obtained by suitably subjecting a specific compound represented by formula (I) to halogen substitution in the presence of a suitable catalyst such as Pd/C and in the presence or absence of base. Suitable methods for preparing other tritium-labeled compounds can be referred to in the literature in the form of Isotopes in the Physical and Biomedical Sciences, Vol 1, Labeled Compounds (Part A), Chapter 6 (1987). In addition, $^{14}C$-labeled compounds can be prepared by using a raw material having $^{14}C$ carbon.

The present invention includes salts capable of being formed by the compound represented by formula (I). Examples of these salts include alkaline metal salts (such as sodium salts, potassium salts or lithium salts), alkaline earth metal salts (such as calcium salts or magnesium salts), other metal salts (such as aluminum salts, iron salts, zinc salts, copper salts, nickel salts or cobalt salts), ammonium salts, amine salts (such as tert-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts or tris(hydroxymethyl)aminomethane salts), salts of inorganic acids (such as hydrohalides including hydrofluorides, hydrochlorides, hydrobromides and hydroiodides, nitrates, perchlorates, sulfates or phosphates), alkylsulfonates (such as methanesulfonates, trifluoromethanesulfonates or ethanesulfonates), aryl sulfonates (such as benzenesulfonate or p-toluenesulfonate), salts of organic acids (such as acetates, malates, fumarates, succinates, citrates, tartrates, oxalates or maleates), and amino acid salts (such as glycine salts, lysine salts, arginine salts, ornithine salts, glutamates or aspartates). These salts can be formed by routinely carried out methods.

The compound represented by formula (I) of the present invention, or a salt thereof, may form a solvate (such as a hydrate) and/or crystal polymorph, and the present invention includes each of these types of solvents and crystal polymorphs. A "solvate" may have an arbitrary number of solvent molecules (such as water molecules) coordinated with a compound represented by formula (I). The compound represented by formula (I), or a salt thereof, may absorb moisture and adhered moisture may adhere thereto, or may form a hydrate, by allowing to stand in air. In addition, the compound represented by formula (I), or a salt thereof, may form a crystal polymorph by recrystallization thereof.

The artificial nucleoside of the present embodiment includes, for example, a compound in which $Z^1$ and $Z^2$ in formula (I) are hydrogen atoms. In addition, the artificial nucleotide of the present embodiment includes, for example, a compound in which $Z^2$ in formula (I) is a phosphorous-containing group.

[Artificial Oligonucleotide]

The artificial oligonucleotide of the present embodiment is an artificial oligonucleotide, or pharmaceutically acceptable salt thereof, that contains one or more nucleoside structures represented by the following formula (II).

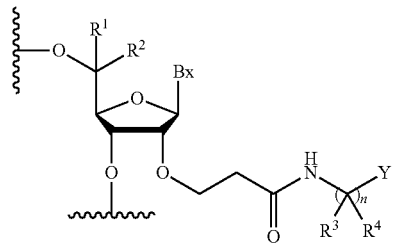

(II)

Bx represents a purin-9-yl group, 2-oxo-pyrimidin-1-yl group or 2-thioxo-pyrmidin-1-yl group. The purin-9-yl group, 2-oxo-pyrmidin-1-yl group and 2-thioxo-pyrmidin-1-yl group are unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group.

$R^1$, $R^2$, $R^3$ and $R^4$, independently of each other, represent a hydrogen atom, halogen atom, cyano group, C1-6 alkyl group or C2-6 alkenyl group. The C1-6 alkyl group and C2-6 alkenyl group are unsubstituted or substituted with one or more substituents solely or differently selected from the group consisting of a halogen atom, C1-6 alkoxy group and cyano group.

Y represents $NR^5R^6$ or a C2-9 aromatic heterocyclic group. $R^5$ and $R^6$ in $NR^5R^6$, independently of each other, represent a hydrogen atom, C1-6 alkyl group, C2-6 alkenyl group (wherein, the C1-6 alkyl group and C2-6 alkenyl group are unsubstituted or substituted with one or more substituents solely or differently selected from the group consisting of a halogen atom, cyano group, nitro group, amino group, hydroxyl group, carboxy group, carbamoyl group, C1-6 alkoxy group, C2-6 alkenyloxy group, C1-6 alkoxycarbonyl group, C2-6 alkenyloxycarbonyl group, C1-6 alkylcarbonyl group, C1-6 alkylamino group, C1-6 alkylaminocarbonyl group, C1-6 alkylcarbonyloxy group, C1-6 alkylcarbonylamino group and C1-6 alkoxycarbonylamino group), or C7-10 aralkyl group (wherein, the C7-10 aralkyl group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group), or $R^5$ and $R^6$, together with a nitrogen atom bound thereto, form a 3- to 11-membered nitrogen-containing non-aromatic heterocyclic group (wherein, the 3- to 11-membered nitrogen-containing non-aromatic heterocyclic group is unsubstituted or is substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group).

In the case Y represents a C2-9 aromatic heterocyclic group, the C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group.

n represents an integer of 1 to 3.

$R^1$ to $R^6$, Bx, Y and n in formula (II) have the same meaning as $R^1$ to $R^6$, Bx, Y and n in formula (I), and preferable aspects thereof are also the same.

The artificial oligonucleotide of the present embodiment contains at least one nucleoside structure represented by formula (II) at an arbitrary location. There are no particular limitations on the number of bases that composes the artificial oligonucleotide, and is, for example, 2 to 50 bases, preferably 8 to 30 bases, more preferably 15 to 25 bases, even more preferably 19 to 23 bases and particularly preferably 19 or 20 bases.

There are no particular limitations on the locations and types of the nucleoside structure represented by formula (II) in the artificial oligonucleotide and can be suitably designed corresponding to the specific objective. For example, the nucleoside structure represented by formula (II) may be contained on the 3'-end or 5'-end of the oligonucleotide. In the case of being contained on the 3'-end, the structure becomes that represented by, for example, the following formula (VI).

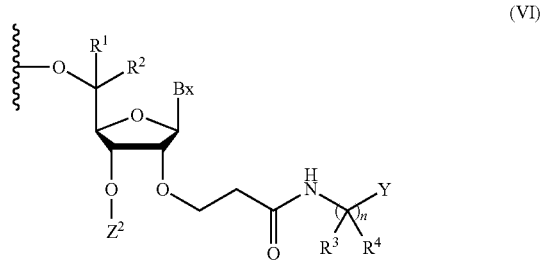

(VI)

$R^1$ to $R^4$, $Z^2$, Bx, Y and n in formula (VI) have the same meanings as $R^1$ to $R^4$, $Z^2$, Bx, Y and n in formula (I).

In addition, in the case of being contained on the 5'-end, the structure becomes that represented by, for example, the following formula (VII).

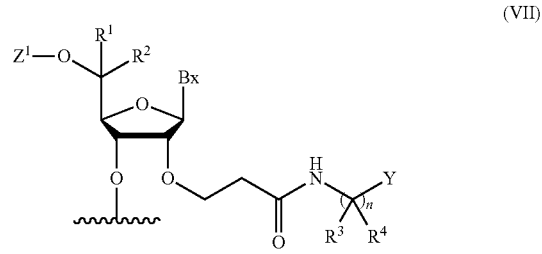

(VII)

$R^1$ to $R^4$, $Z^1$, Bx, Y and n in formula (VII) have the same meanings as $R^1$ to $R^4$, $Z^1$, Bx, Y and n in formula (I).

The 3'-end and/or 5'-end of the artificial oligonucleotide of the present embodiment may be modified. End modification makes it possible to track the oligonucleotide, improve pharmacokinetics or pharmacodynamics of the oligonucleotide, or improve stability or binding affinity of the oligonucleotide. The end-modifying group can be used by suitably selecting from among modifying groups known in the art corresponding to the objective and the like. Examples of end-modifying groups include a hydroxyl group-protecting group, group derived from a reporter gene, group derived from cholesterol, group derived from phospholipid, group derived from a dye molecule and group derived from a fluorescent molecule.

Here, a "derived group" refers to a group formed from a target molecule by removing a hydrogen atom or hydroxyl group and the like therefrom.

In addition, the 3'-position of a nucleotide on the 3'-end of the artificial oligonucleotide of the present embodiment has a hydroxyl group, hydroxyl group substituted with a hydroxyl group-protecting group or hydroxyl group containing a phosphate ester moiety, while the 5'-position of a nucleotide on the 5'-end has a hydroxyl group, hydroxyl group substituted with a hydroxyl group-protecting group or a hydroxyl group containing a phosphate ester moiety. A "phosphate ester moiety" refers to a phosphate ester structure and a terminal phosphate group containing a modified phosphate ester structure. Although the phosphate ester moiety may be located on either end, it is preferably located on the 5'-end.

More specifically, the phosphate ester moiety is group represented by the formula —O—P(=O)(OH)$_2$ or a modifying group thereof. In the modifying group, one or more of the —O— and =O moieties of the phosphate ester moiety may be substituted with a sulfur atom or —N(R$^x$)—, and one or more OH moieties may be substituted with a hydrogen atom, —SH, —N(R$^x$)$_2$ or an alkyl group. Here, Rx represents a hydrogen atom or amino group-protecting group. The 5' and/or 3'-terminal group may also, independently of each other, contain one to three unsubstituted or substituted phosphate ester moieties.

The 5'-positions of nucleotides on the 3'-end and 5'-end of the nucleotide on the 3'-end of the artificial oligonucleotide, independently of each other, preferably represent a hydroxyl group or hydroxyl group containing a phosphate ester moiety, more preferably represent a hydroxyl group, group represented by the formula —O—P(=O)(OH)$_2$, cyanoethoxy(diisopropylamino)phosphino group or hydroxyphosphinyl group, and particularly preferably represent a hydroxyl group.

The artificial oligonucleotide of the present embodiment may have a nucleotide structure in which at least one of a base moiety, sugar moiety and phosphate ester moiety has been modified even if other moieties have a naturally-occurring nucleotide structure provided it contains at least one nucleoside structure represented by formula (II).

For example, although an example of the phosphate ester moiety of the artificial oligonucleotide is a phosphodiester bond possessed by a naturally-occurring nucleic acid, it is not limited thereto, but rather may also be a modified phosphodiester bond. Examples of modifications of phosphodiester bonds include phosphorothioation, methyl phosphonation, chiral methyl phosphonation, phosphodithioation, phosphoroamidation and boranophosphation.

A base moiety other than the nucleoside structure represented by formula (II) in the artificial oligonucleotide may be any arbitrary nucleic acid base defined for the aforementioned Bx.

Examples of nucleosides having a sugar moiety other than the nucleoside structure represented by formula (II) in the artificial oligonucleotide include naturally-occurring ribose or deoxyribose and modified ribose or deoxyribose. Examples of known modifications include the nucleotides disclosed in Japanese Unexamined Patent Publication No. H10-304889, International Publication No. WO 2005/021570, Japanese Unexamined Patent Publication No. H10-195098, Japanese Translation of PCT International Application Publication No. 2002-521310, International Publication No. 2007/143315, International Publication No. WO 2008/043753, International Publication No. WO 2008/029619, International Publication No. WO 2008/049085 and International Publication No. WO 2011/052436. The aforementioned publications disclose the following nucleotides: hexitol nucleic acids (HNA), cyclohexene nucleic acids (CeNA), peptide nucleic acids (PNA), glycol nucleic acids (GNA), threose nucleic acids (TNA), morpholino nucleic acids, tricyclo-DNA (tcDNA), 2'-O-methyl nucleosides, 2'-O-methoxyethyl (2'-MOE) nucleotides, 2'-O-(aminopropyl) (2'-AP) nucleotides, 2'-fluoronucleotides, 2'-F-arabinonucleotides (2'-F-ANA), 4'-CH$_2$—O-2' nucleotides (LNA, locked nucleic acid), bridged nucleic acids (BNA) and 2'-O-methylcarbamoylethyl (MCE) nucleotides.

The sugar moiety of a nucleoside other than the nucleoside structure represented by formula (II) in the artificial oligonucleotide is preferably independently selected from the group consisting of ribose, deoxyribose, 2'-O-methyl ribose, 2'-O-methylcarbamoylethyl ribose, 2'-O-methoxyethyl ribose and 4'-CH$_2$—O-2' nucleotide, more preferably independently selected from the group consisting of deoxyribose, 2'-O-methyl ribose, 2'-O-methylcarbamoylethyl ribose and 2'-O-methoxyethyl ribose, and even more preferably independently selected from deoxyribose and 2'-O-methyl ribose.

In addition, bonds between nucleosides contained in the artificial oligonucleotide may be bonds that do not contain phosphorous atoms provided they are bonds known in the art. Examples of bonds between nucleosides include, but are not limited to, alkanediyl groups, divalent groups derived from non-aromatic carbocyclic rings, haloalkanediyl groups and divalent groups derived from non-aromatic carbocyclic rings substituted with halogens. Examples of bonds between nucleosides include divalent groups derived from siloxane, sulfide groups, sulfoxide groups, sulfone groups, divalent groups derived from acetyl groups, divalent groups derived from alkenyl groups, divalent groups derived from sulfamate groups, methyleneimino groups, methylenehydrazino groups, divalent groups derived from sulfonate groups, sulfonamide groups and amide groups.

Here, an alkanediyl group refers to a divalent substituent in which two hydrogen atoms at arbitrary locations have been removed from a linear or branched saturated hydrocarbon having 1 to 30 carbon atoms. Examples of alkanediyl groups include a methylene group, ethylene group (ethanediyl group), propane-1,3-diyl group, propane-2,2-diyl group, 2,2-dimethylpropane-1,3-diyl group, hexane-1,6-diyl group and 3-methylbutane-1,2-diyl group.

A haloalkanediyl group refers to a group obtained by substituting a hydrogen atom at an arbitrary location of the aforementioned alkanediyl group with one or more of the aforementioned halogen atoms.

A non-aromatic carbocyclic ring refers to an aromatic monocyclic ring, condensed ring, spiro ring or bridged ring having 3 to 10 atoms that compose the ring in which all of the atoms that compose the ring are carbon atoms and which may contain a double bond or triple bond in the ring. Examples of non-aromatic carbocyclic rings include cyclopropane, cyclobutane, cyclopentane, cyclohexane, cycloheptane, cyclooctane, cyclohexene, cyclohexadiene, bicyclo [4.4.0]decane and adamantane.

Bonds between nucleosides contained in the artificial oligonucleotide are preferably, independently of each other, selected from the group consisting of phosphodiester bonds, phosphorothioate bonds, methylphosphonate bonds, methylthiophosphonate bonds, phosphodithioate bonds, phosphoroamidate bonds, phosphorodiamidate bonds, phosphoroamidothioate bonds and boranophosphate bonds, and particularly preferably independently selected from the group consisting of phosphodiester bonds and phosphorothioate bonds.

There are cases in which the artificial oligonucleotide of the present embodiment has isomers. In that case, the present embodiment is not limited to a specific isomer, but rather includes all possible isomers (such as keto-enol tautomers, imine-enamine tautomers, diastereomers, optical isomers and rotational isomers), racemates and mixtures thereof.

One or more hydrogen atoms, carbon atoms and/or other atoms of the artificial oligonucleotide can each be substituted with isotopes of hydrogen atoms, carbon atoms and/or other atoms. Examples of such isotopes, preparation methods and the like are the same as those of the previously described artificial nucleoside and artificial nucleotide.

The artificial oligonucleotide of the present embodiment includes a pharmaceutically acceptable salt thereof. Specific examples of these salts, preparation methods and the like are the same as salts of the previously described artificial nucleoside and artificial nucleotide.

The artificial oligonucleotide, or pharmaceutically acceptable salt thereof, may form a solvate (such as a hydrate) and/or crystal polymorph, and the present invention includes each of these types of solvents and crystal polymorphs. Specific examples of solvates are the same as those of the previously described artificial nucleoside and artificial nucleotide.

There are cases in which the artificial oligonucleotide or pharmaceutically acceptable salt thereof form a prodrug, and the present invention includes each of such prodrugs. A prodrug is a derivative of the artificial oligonucleotide having a group that can be chemically or metabolically degraded that is a compound that allows the obtaining of a pharmacologically active artificial oligonucleotide in vivo as a result of solvolysis or under physiological conditions. Prodrugs include compounds that are converted to the artificial oligonucleotide as a result of being subjected to enzymatic oxidation, reduction or hydrolysis and the like under physiological conditions within the body, as well as compounds converted to the artificial oligonucleotide as a result of being hydrolyzed by gastric acid and the like. Methods for selecting and producing suitable prodrug derivatives are described in, for example, Design of Prodrugs, Elsevier, Amsterdam, 1985. There are also cases in which prodrugs per se have activity.

In the case the artificial oligonucleotide, or pharmaceutically acceptable salt thereof, has a hydroxyl group, examples of prodrugs include prodrugs in the manner of acyloxy derivatives and sulfonyloxy derivatives produced by reacting a compound having a hydroxyl group with a suitable acyl halide, suitable acid anhydride, suitable sulfonyl chloride, suitable sulfonyl anhydride or mixed anhydride, or by reacting using a condensing agent. Examples of partial structures of such derivatives include CH$_3$COO—, C$_2$H$_5$COO—, tert-BuCOO—, C$_{15}$H$_{31}$COO—, PhCOO—, (m-NaOOCPh)COO—, NaOOCCH$_2$CH$_2$COO—, CH$_3$CH(NH$_2$)COO—, CH$_3$N(CH$_3$)COO—, CH$_3$SO$_3$—, CH$_3$CH$_2$SO$_3$—, CF$_3$SO$_3$—, CH$_2$FSO$_3$—, CF$_3$CH$_2$SO$_3$—, p-CH$_3$O-PhSO$_3$—, PhSO$_3$— and p-CH$_3$PhSO$_3$—.

The artificial oligonucleotide can be synthesized by ordinary methods using the compound represented by formula (I). For example, the artificial oligonucleotide can easily be synthesized with a commercially available automated nucleic acid synthesizer (such as that manufactured by Applied Biosystems or GeneDesign). Examples of synthesis methods include solid phase synthesis using phosphoroamidite and solid phase synthesis using hydrogen phosphonate. Examples thereof are disclosed in Tetrahedron Letters 22, 1859-1862 (1981) and International Publication No. WO 2011/052436.

In the case Bx in the nucleoside structure represented by formula (II) has a substituent, the substituent is preferably not protected with a protecting group. Examples of Bx include the groups indicated below.

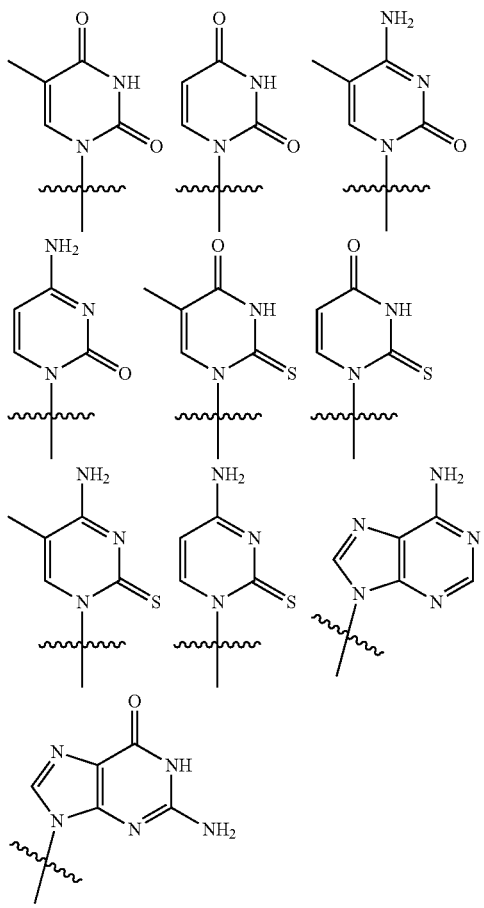

Accordingly, in the case Bx in the compound represented by formula (I) has a substituent protected with a protecting group, de-protection is preferably carried out during oligonucleotide synthesis.

The artificial oligonucleotide demonstrates superior bonding affinity to single-stranded RNA as well as superior nuclease resistance. Thus, the artificial oligonucleotide is thought to demonstrate extremely favorable sustained action in the body. Accordingly, the compound represented by formula (I) of the present embodiment is extremely useful as a material for synthesizing nucleic acid pharmaceuticals such as antisense oligonucleotides. Nucleic acid pharmaceuticals using the artificial oligonucleotide of the present embodiment have higher affinity for a target molecule, are more resistant to degradation in the body, and demonstrate effects with greater stability in comparison with unmodified nucleic acid pharmaceuticals, or in other words, nucleic acid pharmaceuticals derived from naturally-occurring nucleic acids. Expression of a target gene, for example, can be suppressed by creating the artificial oligonucleotide so as to have an expression inhibitory sequence corresponding to the target gene.

There are no particular limitations on the disease able to be treated, prevented or improved by using the artificial oligonucleotide, and examples thereof include metabolic diseases, circulatory diseases, tumors, infections, ophthalmic diseases, inflammatory diseases, autoimmune diseases, hereditary rare diseases, and diseases caused by expression of a gene. Specific examples include hypercholesterolemia, hypertriglyceridemia, spinal muscular atrophy, muscular dystrophy (such as Duchenne muscular dystrophy, myotonic dystrophy, congenital muscular dystrophy (such as Fukuyama-type congenital muscular dystrophy, Ullrich-type congenital muscular dystrophy, merosin-deficient congenital muscular dystrophy, integrin deficiency or Walker Warburg syndrome), Becker muscular dystrophy, limb-girdle muscular dystrophy, Miyoshi muscular dystrophy or facioscapulohumeral dystrophy), Huntington's disease, Alzheimer's disease, transthyretin amyloidosis, familial amyloid cardiomyopathy, multiple sclerosis, Crohn's disease, inflammatory bowel disease, acromegaly, type 2 diabetes, chronic renal disease, RS virus infection, Ebola hemorrhagic fever, Marburg virus, HIV, influenza, hepatitis B, hepatitis C, cirrhosis, chronic cardiac insufficiency, myocardial fibrosis, atrial fibrillation, prostate cancer, melanoma, breast cancer, pancreatic cancer, colon cancer, renal cell carcinoma, cholangiocarcinoma, cervical cancer, liver cancer, lung cancer, leukemia, non-Hodgkin's lymphoma, atopic dermatitis, glaucoma and age-related macular degeneration. The gene causing the aforementioned disease can be set for the aforementioned target gene corresponding to the type of disease, and the aforementioned expression control sequence can be suitably set corresponding to the sequence of the aforementioned target gene. Among the aforementioned diseases, nucleic acid pharmaceuticals using the artificial oligonucleotide are used for Duchenne muscular dystrophy, myotonic dystrophy and Fukuyama-type congenital muscular dystrophy in particular.

Diseases of mammals such as humans as well as various other mammals can be treated, prevented or improved with a nucleic acid pharmaceutical using the artificial oligonucleotide. Although not limited thereto, various diseases of mammals, including rodents (such as mice), cows, sheep, goats, horses, dogs or cats, can be treated. In addition, a nucleic acid pharmaceutical using the artificial oligonucleotide can also be applied to other species such as birds (such as chickens).

Nucleic acid pharmaceuticals using the artificial oligonucleotide can be administered by various methods corresponding to the desired local or systemic treatment, prevention or improvement or corresponding to the region to be treated, prevented or improved. The administration method may be local administration (including ophthalmic, intravaginal, rectal, transnasal and transdermal administration), oral administration or parenteral administration. Examples of parenteral administration include intravenous injection or infusion, subcutaneous administration, intraperitoneal or intramuscular injection, pulmonary administration by aspiration or inhalation, intrathecal administration and intraventricular administration.

In the case of local administration of a nucleic acid pharmaceutical using the artificial oligonucleotide, a preparation such as a transdermal patch, ointment, lotion, cream, gel, dropping agent, suppository, aerosol, liquid or powder can be used.

Examples of compositions for oral administration include powders, granules, suspensions or solutions obtained by dissolving in water or a non-aqueous medium, capsules, powdered preparations and tablets.

Examples of compositions for parenteral, intrathecal or intraventricular administration include sterile aqueous solutions containing buffers, diluents and other suitable additives.

Nucleic acid pharmaceuticals using the artificial oligonucleotide can be obtained by mixing an effective amount of nucleic acid with various types of pharmaceutical additives such as an excipient, binder, wetting agent, disintegration agent, lubricant or diluent suitable for the drug form thereof as necessary. In the case of an injection preparation, the preparation is obtained by carrying out sterilization treatment together with a suitable carrier.

Examples of excipients include lactose, sucrose, glucose, starch, calcium carbonate and crystalline cellulose. Examples of binders include methyl cellulose, carboxymethyl cellulose, hydroxypropyl cellulose, gelatin and polyvinyl pyrrolidone. Examples of disintegration agents include carboxymethyl cellulose, sodium carboxymethyl cellulose, starch, sodium alginate, powdered agar and sodium lauryl sulfate. Examples of lubricants include talc, magnesium stearate and Macrogol. Examples of suppository bases that can be used include cocoa butter, Macrogol and methyl cellulose. In addition, in the case of preparing a liquid agent or emulsified or suspended injection preparation, a normally used solubilizing agent, suspending agent, emulsifier, stabilizer, preservative or isotonic agent and the like may be suitably added. A corrective or aromatic may also be added in the case of oral administration.

Administration is dependent on the severity and responsivity of the disease being treated, and the course of treatment is continued for several days to several months or until a cure is realized or a decline of systems has been achieved. The optimum dosing schedule can be calculated from measurement of drug accumulation in the body. The optimal dose, administration method and repetition frequency can be determined by a person with ordinary skill in the art. Although the optimal dose fluctuates corresponding to the relative efficacy of individual nucleic acid pharmaceuticals, in general, optimal dose can be calculated based on the $IC_{50}$ or $EC_{50}$ value as determined by in vitro and in vivo animal studies. For example, the dose expressed as mg/kg is calculated in accordance with ordinary methods provided the molecular weight of the nucleic acid (derived from the nucleic acid sequence and chemical structure) and, for example, the effective dose is given in the manner of $IC_{50}$ (derived experimentally).

Moreover, the artificial oligonucleotide of the present invention can be administered at a dose level effective for improvement or prevention in order to improve or prevent diseases caused by expression of a target gene.

Although the artificial oligonucleotide according to the present embodiment can be produced according to the method indicated below, the following production method merely indicates one example of an ordinary production method and is not intended to limit the method for producing the artificial oligonucleotide according to the present embodiment.

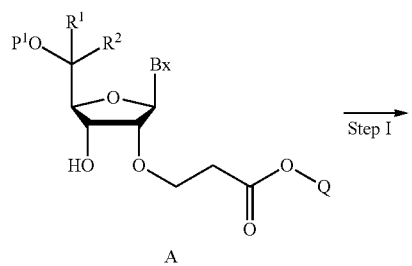

A

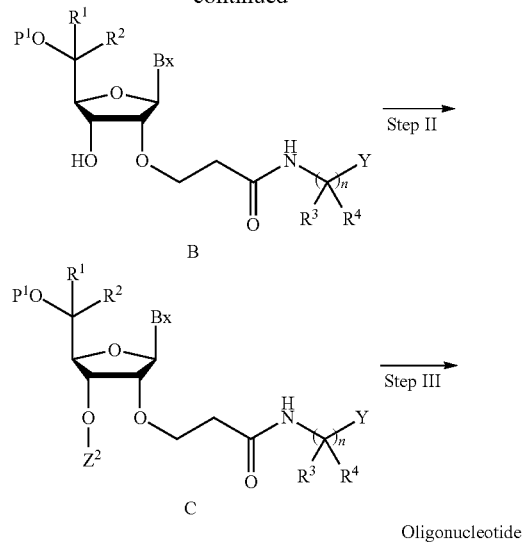

Oligonucleotide

In the above formula, $P^1$ represents a hydroxyl group-protecting group, $Z^2$ represents a phosphorous-containing group, Q represents a hydrogen atom or C1-6 alkyl group, and other symbols are the same as previously defined.

The starting material of Step I in the form of Compound A can be synthesized according to the method described in, for example, Japanese Patent No. 5194256, the Journal of Organic Chemistry, Vol. 76, p. 3042 (2011), or Organic and Biomolecular Chemistry, Vol. 12, p. 6457 (2014). More specifically, the Compound A having a diverse variety of $R^1$, $R^2$ and Bx can be synthesized from Compound A-1 indicated below using a combination of protection/de-protection reactions (such as the reactions described in the aforementioned Protective Groups in Organic Synthesis, $4^{th}$ edition), oxidation reactions or reduction reactions (and for example, Comprehensive Organic Transformations, Second Edition, R. C. Larock, ed., Wiley-VCH Publishing (1999) can be referred to with respect to oxidation reactions and reduction reactions).

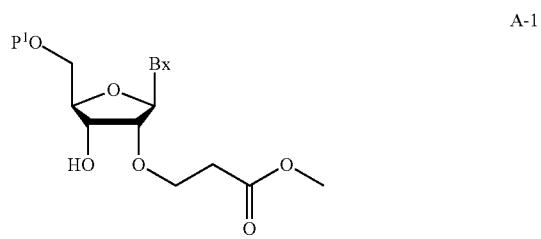

A-1

In the above formula, $P^1$ and Bx are the same as previously defined.

In order to synthesize Compound A in which at least one of $R^1$ and $R^2$ is an alkyl group, for example, the hydroxyl group at the 3'-position is first protected by a hydroxyl group protection/de-protection reaction to obtain a compound in which the hydroxyl group at the 5'-position is de-protected (Compound A-2). Next, the hydroxyl group at the 5'-position of Compound A-2 is oxidized and a desired $R^1$ can be introduced using an alkyl metal reagent or Grignard reagent corresponding to $R^1$. In addition, the other hydroxyl group at the 5'-position can be oxidized as necessary and a desired $R^2$ can be introduced using an alkyl metal reagent or Grignard reagent corresponding to $R^2$. Compound A, in which at least one of $R^1$ and $R^2$ is an alkyl group, can be synthesized by de-protecting the protected hydroxyl group at the 3'-position of the resulting compound.

Compound A-1 having a desired Bx can be synthesized using a ribonucleotide corresponding to the desired Bx according to a method known among persons with ordinary skill in the art such as the method described in Japanese Patent No. 5194256 or the Journal of Organic Chemistry, Vol. 76, p. 3042 (2011). Since the reaction site through synthesis of Compound A from Compound A-1 is spatially located away from Bx, the aforementioned reaction through the synthesis of Compound A from Compound A-1 can be applied to a diverse range of Bx structures.

In addition, Compound A having a diverse range of $R^1$, $R^2$ and Bx can be synthesized from the following Compound A-3 having a diverse range of $R^1$, $R^2$ and Bx according to the method described in Japanese Patent No. 5194256 or the Journal of Organic Chemistry, Vol. 76, p. 3042 (2011). More specifically, Compound A can be obtained by reacting Compound A-3 and an acrylic acid ester (such as methyl acrylate) in a solvent and in the presence of a base (such as cesium carbonate).

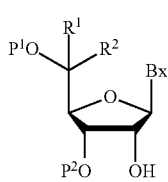

A-3

In the above formula, $P^1$ and $P^2$, independently of each other, represent a hydroxyl group-protecting group and other symbols are the same as previously defined.

Compound A-3 having a diverse range of $R^1$, $R^2$ and Bx can be synthesized from Compound A-4 in the same manner as the previously described method used to synthesize Compound A from Compound A-1. Compound A-4, in which Bx represents a 2-thioxo-pyrimidin-1-yl group (wherein, the 2-thioxo-pyrimidin-1-yl group is unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group), can be synthesized from a compound in which Bx represents the corresponding 2-oxo-pyrimidin-1-yl group according to the method described in Chemical Communications, Vol. 48, p. 7313 (2012).

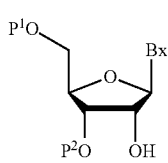

A-4

In the above formula, $P^1$, $P^2$ and Bx are the same as previously defined.

(Step I) Amidation Reaction with Primary Amine

Compound B can be obtained by an ester-amide exchange reaction using a primary alkyl amine in which one or a plurality of $R^3$, one or a plurality of $R^4$ and Y are bound to an alkyl group moiety. An example of an ester-amide exchange reaction is a method in which 1 to 100 equivalents of the primary alkyl amine are dissolved in a solvent.

In addition, Compound B can be obtained by hydrolyzing Compound A to obtain a carboxylic acid derivative according to a method known among persons with ordinary skill in the art followed by reacting the carboxylic acid derivative with a primary alkyl amine in which one or a plurality of $R^3$, one or a plurality of $R^4$ and Y are bound to an alkyl group moiety by a condensation reaction.

For example, after reacting Compound A with 1 to 20 equivalents of a base such as sodium hydroxide or potassium hydroxide in an alcohol solvent to obtain a carboxylic acid derivative, the carboxylic acid derivative is reacted with 1 to 10 equivalents of the primary alkyl amine in the presence of 1-ethyl-3-(3-dimethylaminopropyl)carbodiimide hydrochloride and 1-hydroxybenzotriazole in a solvent.

(Step II) Phosphorylation Reaction

Compound C can be obtained by phosphorylating a hydroxyl group of Compound B by a reaction known among persons with ordinary skill in the art (such as a reaction using a mono-substituted chloro(alkoxy)phosphine or di-substituted alkoxyphosphine). Specific examples of the phosphorylation reaction include a method in which 2-cyanoethyldiisopropylchlorophosphoroamidite is reacted in a solvent, and a method in which tris-(1,2,4-triazolyl)phosphite is reacted in a solvent.

Since the reaction sites of the phosphorylation reaction consist of hydroxyl groups spatially separated from $R^1$, $R^2$, $R^3$, $R^4$, Y and Bx, the aforementioned phosphorylation reaction can be applied to a diverse range of structures of $R^1$, $R^2$, $R^3$, $R^4$, Y and Bx.

Furthermore, Compound B may also be obtained by a different method from that of Step I. Compound B can be synthesized according to a method known among persons with ordinary skill in the art using for the starting material a known ribonucleoside or derivative thereof (such as a derivative in which an amino group of a base moiety is substituted with an amino group-protecting group and/or a portion of the hydroxyl groups of a sugar moiety is substituted with hydroxyl group-protecting groups). Specific examples of methods differing from Step I are described in Examples 4-2 to 4-6 to be subsequently described.

The artificial oligonucleotide can be synthesized with an automated nucleic acid synthesizer (such as the nS-8II (manufactured by GeneDesign)) using commercially available phosphoroamidite reagents required to produce oligonucleotide analogues of Compound C and a desired nucleotide sequence.

EXAMPLES

Although the following provides a detailed explanation of the present invention by listing examples thereof, the present invention is not limited thereto. Furthermore, in the examples, NMR refers to the nuclear magnetic resonance spectrum and MS refers to mass spectrometry.

In cases in which $^1$H-NMR data is shown, measurements were made at 500 MHz (using the Varian AS500 manufactured by Varian) and data represents the chemical shift δ (units: ppm) of signals obtained by using as the internal standard a signal derived from tetramethylsilane or a measurement solvent. "s" indicates a singlet, "d" a doublet, "t"

a triplet, "m" a multiplet, "brs" a broad singlet, "dd" a doublet of doublets, "dt" a doublet of triplet, "dq" a double of quartet, "ddd" a doublet or doublet of doublet, "ddt" a doublet of doublet of triplet, "CDCl$_3$" refers to deuterated chloroform, "DMSO-d$_6$" refers to deuterated dimethyl sulfoxide, and "Bz" refers to benzoyl.

In cases in which $^{13}$C-NMR data is shown, measurements were made at 125 MHz (using the Varian AS500 manufactured by Varian) and data represents the chemical shift δ (units: ppm) of signals obtained by using the signal derived from the measurement solvent for the internal standard.

In cases in which $^{31}$P-NMR data is shown, measurements were made at 202 MHz (using the Varian AS500 manufactured by Varian) and data represents the chemical shift δ (units: ppm) of signals obtained by using phosphoric acid for the internal standard.

Unless specifically indicated otherwise, MS measurements were carried out using electrospray ionization (ESI) under Conditions 1 indicated below. "ESI$^+$" refers to the ESI positive ion mode while "ESI$^-$" refers to the ESI negative ion mode.

Conditions 1:
Instrument: Bruker MicroTOF II
Measurement solvent: Methanol
Measurement mode: Cation or anion MS measurements using MALDI-TOF-MASS measurement were carried out under Conditions 2 indicated below.

Conditions 2:
Instrument: Bruker UltrafleXtreme
Matrix: Saturated 3-hydroxypicolinic acid acetonitrile solution containing 10 mg/mL of diammonium hydrogen citrate
Target plate: MTP 384 target plate, polished steel BC
Measurement mode: Linear+cation Unless specifically indicated otherwise, purification by silica gel column chromatography was carried out using Silica Gel N60 manufactured by Kanto Chemical.

Example 1

Synthesis of Nucleoside Analogue: (2R,3R,4R,5R)-2-([bis(4-methoxyphenyl)(phenyl)methoxy]methyl)-5-(5-methyl-2,4-dioxo-3,4-dihydropyrimidin-1(2H)-yl)-4-(3-oxo-3-((2-(pyridin-2-yl)ethyl)amino)propoxy)tetrahydrofuran-3-yl(2-cyanoethyl)diisopropylphosphoroamidite (Compound 3)

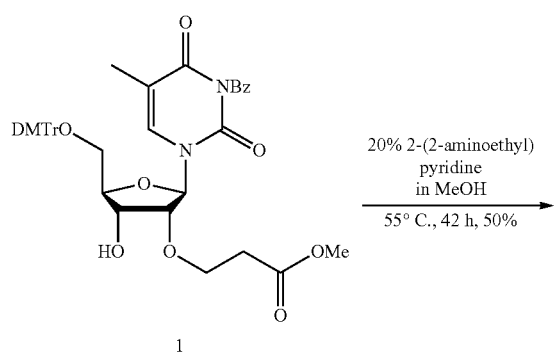

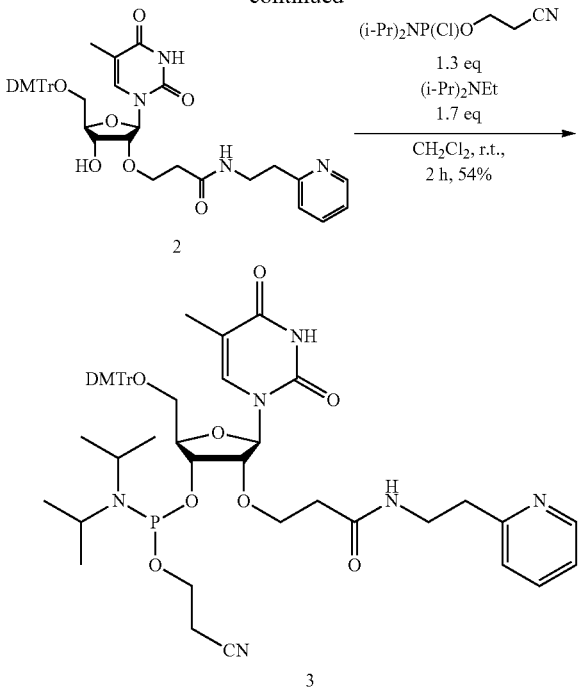

Example 1-1 Synthesis of Compound 2

Compound 1 (synthesized according to the method described in Organic and Biomolecular Chemistry, Vol. 12, p. 6457 (2014)) (150 mg, 0.2 mmol) was dissolved in anhydrous methanol (1.6 ml). 2-(2-aminoethyl)pyridine (0.4 ml) was added to that solution and allowed to react for 42 hours at 55° C. Following the reaction, a saturated aqueous sodium bicarbonate solution was added followed by extraction with ethyl acetate. The organic layer was recovered and dried with anhydrous sodium sulfate followed by distilling off the solvent under reduced pressure. The resulting residue was purified by silica gel column chromatography (developing solvent: dichloromethane-methanol) to obtain Compound 2 (73 mg, yield: 50%).

MS (ESI): [M−H]$^-$ 735.3022.

$^1$H NMR (CDCl$_3$, 500 MHz): δ 1.34 (1H, s), 2.29-2.56 (2H, m), 2.90-3.03 (2H, m), 3.35-3.51 (2H, m), 3.52-3.62 (2H, m), 3.63-3.85 (8H, m), 3.90-3.96 (1H, m), 4.02 (1H, t, J=4.7), 4.07-4.15 (1H, m), 4.50 (1H, t, J=4.8), 5.02-5.19 (1H, brs), 6.01 (1H, d, J=4.6), 6.81 (1H, d, J=8.4), 7.11-7.25 (4H, m), 7.27-7.43 (9H, m), 7.55-7.66 (2H, m), 8.54 (1H, d, J=5.0), 10.48-10.60 (1H, brs).

$^{13}$C NMR (CDCl$_3$, 125 MHz): δ 171.5, 164.5, 159.3, 158.8, 158.8, 151.0, 148.8, 144.4, 137.3, 135.6, 135.5, 135.4, 130.2, 128.3, 128.1, 127.2, 123.7, 122.0, 113.4, 111.2, 87.0, 84.0, 82.5, 77.4, 77.2, 76.9, 69.5, 66.0, 63.0, 55.4, 55.3, 39.5, 36.8, 35.7, 11.9.

Example 1-2 Synthesis of Compound 3

Compound 2 (73 mg, 0.1 mmol) was dehydrated by azetropy with anhydrous pyridine, anhydrous toluene and anhydrous dichloromethane solution followed by dissolving in anhydrous dichloromethane (1 ml). N,N-diisopropylethylamine (30 μl, 0.13 mmol) and 2-cyanoethyldiisopropylchlorophosphoroamidite (30 μl, 0.17 mmol) were added to that solution and allowed to react for 2 hours at room temperature. Following the reaction, a saturated aqueous sodium bicarbonate solution was added followed by extraction with dichloromethane. The organic layer was dried with anhydrous sodium sulfate and the solvent was distilled off under reduced pressure. The resulting residue was purified by silica gel column chromatography (developing solvent: dichloromethane-methanol) to obtain Compound 3 (50 mg, yield: 54%).

MS (ESI): [M+Na]$^+$ 959.4079.

$^1$H NMR (CDCl$_3$, 500 MHz): δ 0.87-0.97 (3H, m), 0.99-1.13 (9H, m), 1.27-1.42 (3H, m), 2.21-2.32 (1H, m), 2.33-2.47 (2H, m), 2.50-2.63 (1H, m), 2.80-2.94 (1H, m), 3.00-3.14 (1H, m), 3.17-3.29 (1H, m), 3.32-4.05 (17H, m), 4.07-4.26 (1H, m), 4.29-4.43 (1H, m), 5.81-6.03 (1H, m), 6.63-6.89 (5H, m), 7.00-7.24 (8H, m), 7.29-7.41 (2H, m), 7.46-7.56 (1H, m), 7.56-7.68 (1H, m), 8.41-8.59 (1H, m), 9.86-10.78 (1H, m).

$^{13}$C NMR (CDCl$_3$, 125 MHz): δ 171.2, 171.1, 164.1, 164.1, 159.3, 159.3, 158.8, 151.0, 149.2, 144.3, 144.2, 136.8, 136.8, 135.4, 135.4, 135.3, 135.0, 134.9, 130.2, 128.4, 128.3, 128.1, 127.3, 123.5, 121.7, 117.9, 117.5, 113.4, 111.5, 87.7, 87.6, 87.1, 87.0, 83.7, 83.2, 82.6, 82.1, 77.4, 77.2, 76.9, 70.8, 70.7, 70.6, 70.5, 67.8, 67.3, 62.4, 62.2, 58.7, 58.5, 57.9, 57.7, 55.4, 55.4, 55.3, 43.4, 43.3, 43.3, 43.2, 39.6, 39.5, 37.4, 37.3, 24.8, 24.8, 24.7, 24.7, 24.6, 20.6, 20.5, 20.3, 20.2, 12.0, 11.9.

$^{31}$P NMR (CDCl$_3$, 202 MHz): δ 151.0, 150.7.

Example 2

Synthesis of Nucleoside Analogue: (2R,3R,4R,5R)-2-([bis(4-methoxyphenyl)(phenyl)methoxy]methyl)-4-(3-((2-(dimethylamino)ethyl)amino)-3-oxo-propoxy)-5-(5-methyl-2,4-dioxo-3,4-dihydropyrimidin-1(2H)-yl) tetrahydrofuran-3-yl(2-cyanoethyl)diisopropylphosphoroamidite (Compound 5)

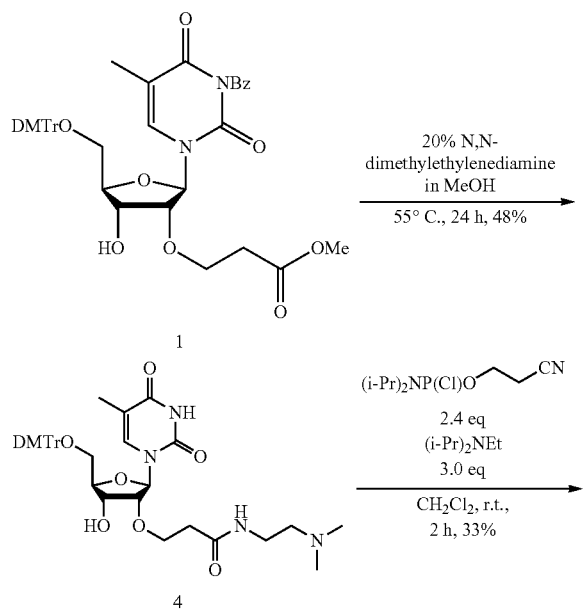

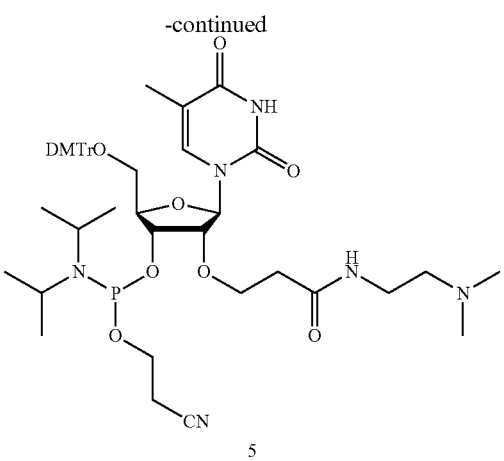

Example 2-1 Synthesis of Compound 4

N,N-dimethylethylenediamine (1.7 ml, 15.6 mmol) was added to a methanol (6.8 ml) solution of Compound 1 (synthesized according to the method described in Organic and Biomolecular Chemistry, Vol. 12, p. 6457 (2014)) (660 mg, 0.85 mmol) followed by stirring for 24 hours at 55° C. Following the reaction, water was added followed by extraction with dichloromethane. The organic layer was dried with anhydrous sodium sulfate and the solvent was distilled off under reduced pressure. The resulting residue was purified by silica gel column chromatography (developing solvent: dichloromethane-methanol) to obtain Compound 4 (286 mg, yield: 48%).

MS (ESI): [M+H]$^+$ 703.3331.

$^1$H NMR (CDCl$_3$, 500 MHz): δ 1.38 (3H, s), 2.23 (6H, s), 2.33 (1H, d, J=16.3), 2.38-2.68 (3H, m), 3.21-3.32 (1H, m), 3.36-3.59 (3H, m), 3.71-3.89 (7H, m), 3.96-4.10 (2H, m), 4.13-4.18 (1H, m), 4.55 (1H, t, J=4.6), 6.04 (1H, d, J=4.6), 6.84 (4H, d, J=8.5), 7.26-7.33 (7H, m), 7.38-7.44 (2H, m), 7.65 (1H, s).

$^{13}$C NMR (CDCl$_3$, 125 MHz): δ 171.6, 164.5, 158.8, 158.8, 152.1, 144.5, 135.5, 135.4, 135.3, 130.2, 130.2, 128.2, 128.1, 127.3, 113.4, 111.8, 87.1, 86.7, 84.5, 83.1, 69.6, 65.7, 63.3, 57.6, 55.4, 44.3, 36.7, 34.8, 11.9.

Example 2-2 Synthesis of Compound 5

Compound 4 (960 mg, 1.37 mmol) was dehydrated by azetropy with anhydrous pyridine, anhydrous toluene and anhydrous dichloromethane solution followed by dissolving in anhydrous dichloromethane (13.4 ml). N,N-diisopropyl-ethylamine (690 μl, 4.0 mmol) and 2-cyanoethyldiisopropylchlorophosphoroamidite (730 μl, 3.3 mmol) were added to that solution and allowed to react for 2 hours at room temperature. Following the reaction, a saturated aqueous sodium bicarbonate solution was added followed by extraction with dichloromethane. The organic layer was dried with anhydrous sodium sulfate and the solvent was distilled off under reduced pressure. The resulting residue was purified by silica gel column chromatography (developing solvent: dichloromethane-methanol) to obtain Compound 5 (408 mg, yield: 33%).

MS (ESI): [M+H]$^+$ 903.4401.

$^1$H NMR (CDCl$_3$, 500 MHz): δ 0.95-1.03 (3H, m), 1.11-1.20 (9H, m), 1.33-1.40 (3H, m), 2.18-2.26 (6H, m), 2.33-2.57 (5H, m), 2.62-2.70 (1H, m), 3.24-3.39 (3H, m), 3.46-3.69 (4H, m), 3.73-3.83 (7H, m), 3.85-4.15 (3H, m), 4.17-4.31 (1H, m), 4.43-4.55 (1H, m), 5.99-6.07 (1H, m), 6.60-6.74 (1H, m), 6.76-6.91 (4H, m), 7.27-7.35 (7H, m), 7.37-7.46 (2H, m), 7.64-7.73 (1H, m).

$^{13}$C NMR (CDCl$_3$, 125 MHz): δ 171.0, 170.9, 164.1, 164.1, 158.9, 151.0, 150.9, 144.4, 144.3, 135.4, 135.4, 135.4, 135.3, 135.3, 130.4, 130.3, 128.5, 128.4, 128.1, 128.1, 127.3, 118.0, 117.6, 113.4, 111.5, 111.3, 88.1, 88.1, 87.1, 87.0, 83.0, 82.9, 82.3, 81.6, 70.8, 70.7, 70.6, 67.8, 67.4, 62.3, 61.9, 58.7, 58.6, 58.1, 58.0, 57.8, 55.4, 55.4, 55.4, 45.1, 45.1, 43.5, 43.4, 43.3, 43.2, 37.2, 37.1, 24.8, 24.8, 24.7, 24.7, 20.6, 20.6, 20.4, 20.3, 11.9, 11.9.

$^{31}$P NMR (CDCl$_3$, 202 MHz): δ 150.8, 150.5.

Example 3

Synthesis of Nucleoside Analogue: (2R,3R,4R,5R)-2-([bis(4-methoxyphenyl)(phenyl)methoxy]methyl)-5-(5-methyl-2,4-dioxo-3,4-dihydropyrimidin-1(2H)-yl)-4-(3-(2-morpholinoethyl)amino)-3-oxopropoxy)tetrahydrofuran-3-yl(2-cyanoethyl) diisopropylphosphoroamidite (Compound 7)

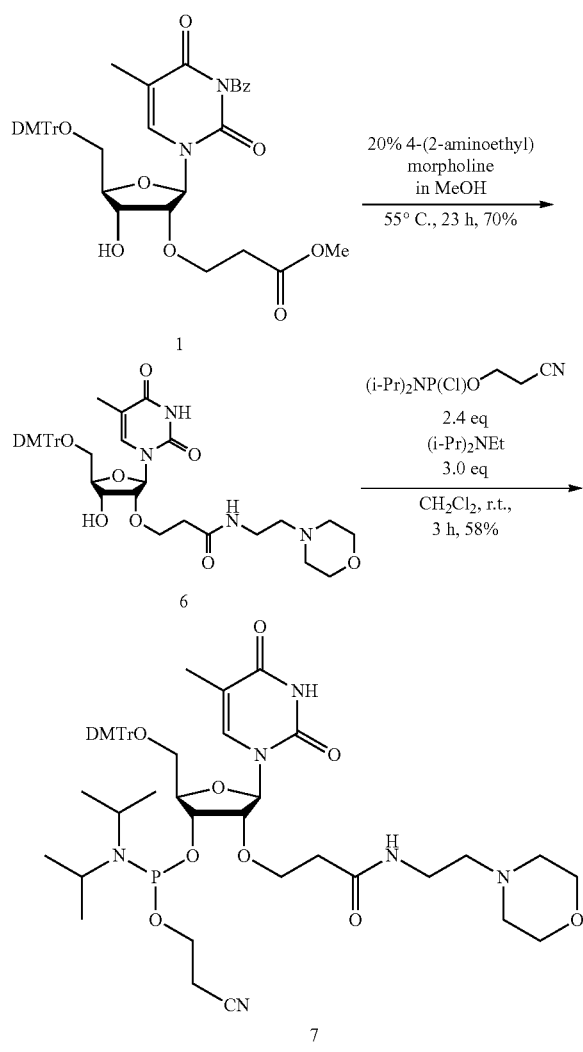

Example 3-1 Synthesis of Compound 6

4-(2-aminoethyl)morpholine (1.7 ml, 15.6 mmol) was added to a methanol (2.2 ml) solution of Compound 1 (synthesized according to the method described in Organic and Biomolecular Chemistry, Vol. 12, p. 6457 (2014)) (200 mg, 0.27 mmol) followed by stirring for 23 hours at 55° C. Following the reaction, water was added followed by extraction with dichloromethane. The organic layer was dried with anhydrous sodium sulfate and the solvent was distilled off under reduced pressure. The resulting residue was purified by silica gel column chromatography (Aminosilica NH, Fuji Silysia Chemical, developing solvent:dichloromethane-methanol) to obtain Compound 6 (140 mg, yield: 70%).

MS (ESI): [M+H]$^+$ 745.3431.

$^1$H NMR (CDCl$_3$, 500 MHz): δ 1.36 (3H, s), 2.25-2.70 (8H, m), 3.26-3.56 (4H, m), 3.61-3.75 (4H, m), 3.75-3.89 (7H, m), 4.01-4.12 (2H, m), 4.12-4.23 (1H, m), 4.58 (1H, t, J=4.4), 4.65-5.15 (1H, brs), 6.07 (1H, d, J=5.1), 6.71 (1H, t, J=5.3), 6.84 (5H, d, J=8.9), 7.26-7.33 (6H, m), 7.35-7.44 (2H, m), 7.66 (1H, s), 9.05-9.57 (1H, brs).

$^{13}$C NMR (CDCl$_3$, 125 MHz): δ 171.4, 163.9, 158.9, 158.8, 151.4, 144.4, 135.5, 135.4, 135.3, 130.2, 130.2, 128.2, 128.1, 127.3, 113.4, 111.7, 87.2, 86.5, 86.5, 84.4, 82.7, 77.4, 77.2, 76.9, 69.5, 66.5, 65.7, 63.3, 57.6, 55.4, 55.4, 53.4, 35.4, 35.2, 11.8.

Example 3-2 Synthesis of Compound 7

Compound 6 (270 mg, 0.36 mmol) was dehydrated by azetropy with anhydrous pyridine, anhydrous toluene and anhydrous dichloromethane solution followed by dissolving in anhydrous dichloromethane (3.6 ml). N,N-diisopropylethylamine (190 μl, 1.1 mmol) and 2-cyanoethyldiisopropylchlorophosphoroamidite (190 μl, 0.85 mmol) were added to that solution and allowed to react for 3 hours at room temperature. Following the reaction, a saturated aqueous sodium bicarbonate solution was added followed by extraction with dichloromethane. The organic layer was dried with anhydrous sodium sulfate and the solvent was distilled off under reduced pressure. The resulting residue was purified by silica gel column chromatography (developing solvent: dichloromethane-methanol) to obtain Compound 7 (200 mg, yield: 58%).

MS (ESI): [M+H]$^+$ 945.4496.

$^1$H NMR (CDCl$_3$, 500 MHz): δ 0.90-1.05 (2H, m), 1.06-1.24 (10H, m), 1.27-1.42 (3H, m), 2.17-2.77 (11H, m), 3.25-3.60 (6H, m), 3.60-4.00 (12H, m), 4.00-4.16 (2H, m), 4.16-4.33 (1H, m), 4.42-4.59 (1H, m), 5.95-6.12 (1H, m), 6.62-6.92 (5H, m), 7.27-7.36 (6H, m), 7.37-7.49 (2H, m), 7.65-7.86 (1H, m), 9.41-9.91 (1H, brs).

$^{13}$C NMR (CDCl$_3$, 125 MHz): δ 171.0, 163.9, 158.9, 150.7, 150.6, 144.3, 144.3, 135.4, 135.3, 135.2, 130.4, 130.3, 128.4, 128.4, 128.1, 128.1, 127.4, 127.3, 117.9, 117.6, 113.5, 113.2, 111.3, 111.3, 88.7, 88.6, 88.5, 88.4, 87.1, 87.0, 82.9, 82.7, 82.4, 82.2, 81.7, 81.5, 77.4, 77.2, 76.9, 70.6, 70.4, 68.0, 67.7, 67.0, 61.8, 57.5, 57.5, 55.5, 55.5, 55.3, 55.3, 53.5, 43.4, 43.3, 37.2, 36.0, 24.8, 24.7, 20.6, 20.6, 20.4, 20.3, 11.9, 11.9. $^{31}$P NMR (CDCl$_3$, 202 MHz): δ 150.9, 150.2.

Example 4

Synthesis of Nucleoside Analogue: (2R,3R,4R,5R)-4-(3-((2-(1H)benzo[d]imidazol-1-yl)ethyl)amino)-3-oxopropoxy)-((bis(4-methoxyphenyl)(phenyl)methoxy)methyl)-5-(5-methyl-2,4-dioxo-3,4-dihydropyrimidin-1(2H)-yl)-tetrahydrofuran-3-yl(2-cyanoethyl)diisopropylphosphoroamidite (Compound 9)

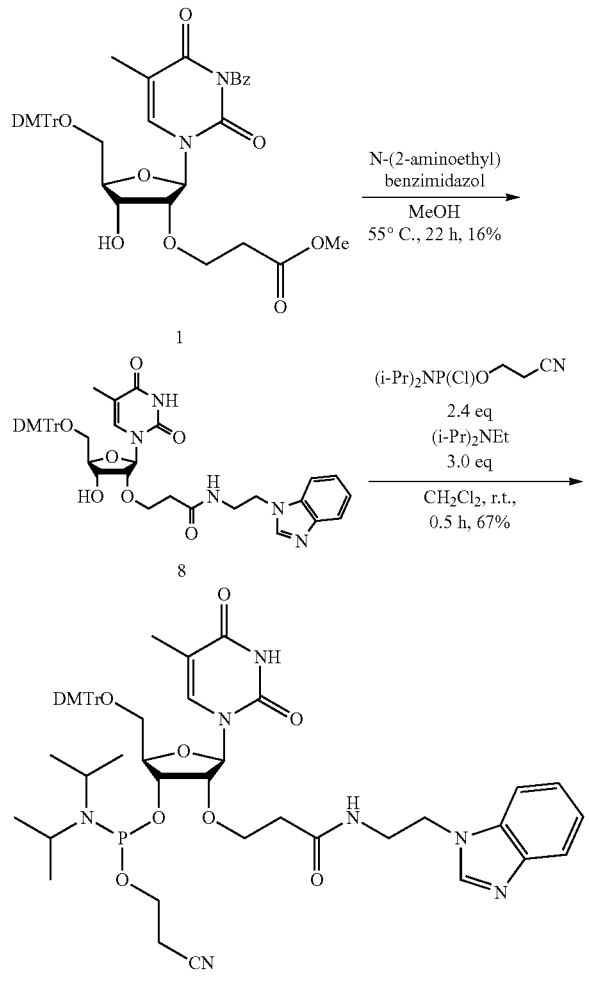

Example 4-1 Synthesis of Compound 9

N-(2-aminoethyl)benzimidazole (8.3 g, 50.4 mmol) was added to a methanol (14 ml) solution of Compound 1 (synthesized according to the method described in Organic and Biomolecular Chemistry, Vol. 12, p. 6457 (2014)) (1.1 g, 1.4 mmol) followed by stirring for 22 hours at 55° C. Following the reaction, water was added followed by extraction with dichloromethane. The organic layer was dried with anhydrous sodium sulfate and the solvent was distilled off under reduced pressure. The resulting residue was purified by silica gel column chromatography (developing solvent: dichloromethane-methanol) to obtain Compound 8 (170 mg, yield: 16%).

The resulting Compound 8 (170 mg, 0.22 mmol) was dehydrated by azetropy with anhydrous pyridine, anhydrous toluene and anhydrous dichloromethane solution followed by dissolving in anhydrous dichloromethane (2.2 ml). N,N-diisopropylethylamine (113 μl, 0.66 mmol) and 2-cyanoethyldiisopropylchlorophosphoroamidite (118 μl, 0.53 mmol) were added to that solution and allowed to react for 0.5 hours at room temperature. Following the reaction, a saturated aqueous sodium bicarbonate solution was added followed by extraction with dichloromethane. The organic layer was dried with anhydrous sodium sulfate and the solvent was distilled off under reduced pressure. The resulting residue was purified by silica gel column chromatography (Amino-silica NH, Fuji Silysia Chemical, developing solvent:dichloromethane-methanol) to obtain Compound 9 (143 mg, yield: 67%).

MS (ESI): [M+H]$^+$ 976.4372.

$^1$H NMR (CDCl$_3$, 500 MHz): δ 0.94-1.16 (3H, m), 1.08-1.16 (9H, m), 1.29-1.35 (3H, m), 2.27-2.61 (4H, m), 3.24-3.29 (1H, m), 3.38-3.85 (16H, m), 3.92-4.48 (7H, m), 5.66-5.70 (1H, m), 6.80-6.96 (4H, m), 6.96-7.06 (1H, m), 7.23-7.48 (22H, m), 7.64-7.70 (1H, m), 7.75-7.81 (1H, m), 7.91-7.95 (1H, m), 8.34-8.43 (1H, m).

$^{13}$C NMR (CDCl$_3$, 125 MHz): δ 172.0, 171.8, 164.0, 163.9, 158.9, 158.8, 150.9, 150.7, 144.4, 144.2, 143.8, 143.5, 135.4, 135.3, 135.0, 134.9, 130.5, 130.3, 128.5, 128.3, 128.2, 128.0, 123.1, 123.0, 122.3, 122.2, 120.4, 120.2, 118.0, 117.9, 117.7, 117.6, 113.4, 113.2, 111.4, 111.3, 109.9, 109.8, 89.1, 89.0, 88.9, 88.8, 87.0, 86.9, 82.4, 82.2, 77.1, 70.7, 70.5, 70.3, 70.0, 67.8, 67.5, 67.2, 61.6, 61.5, 61.3, 61.2, 58.1, 58.0, 57.9, 57.8, 55.5, 55.3, 44.3, 44.1, 43.4, 43.3, 43.2, 43.1, 39.4, 39.3, 39.3, 39.2, 37.1, 36.9, 25.0, 24.5, 20.6, 20.5, 20.4, 20.2, 12.0, 11.8.

$^{31}$P NMR (CDCl$_3$, 202 MHz): δ 150.2, 150.8.

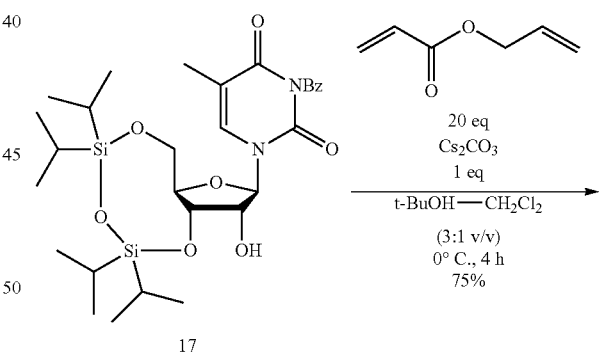

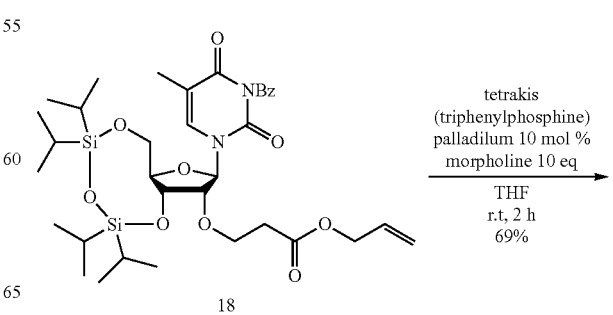

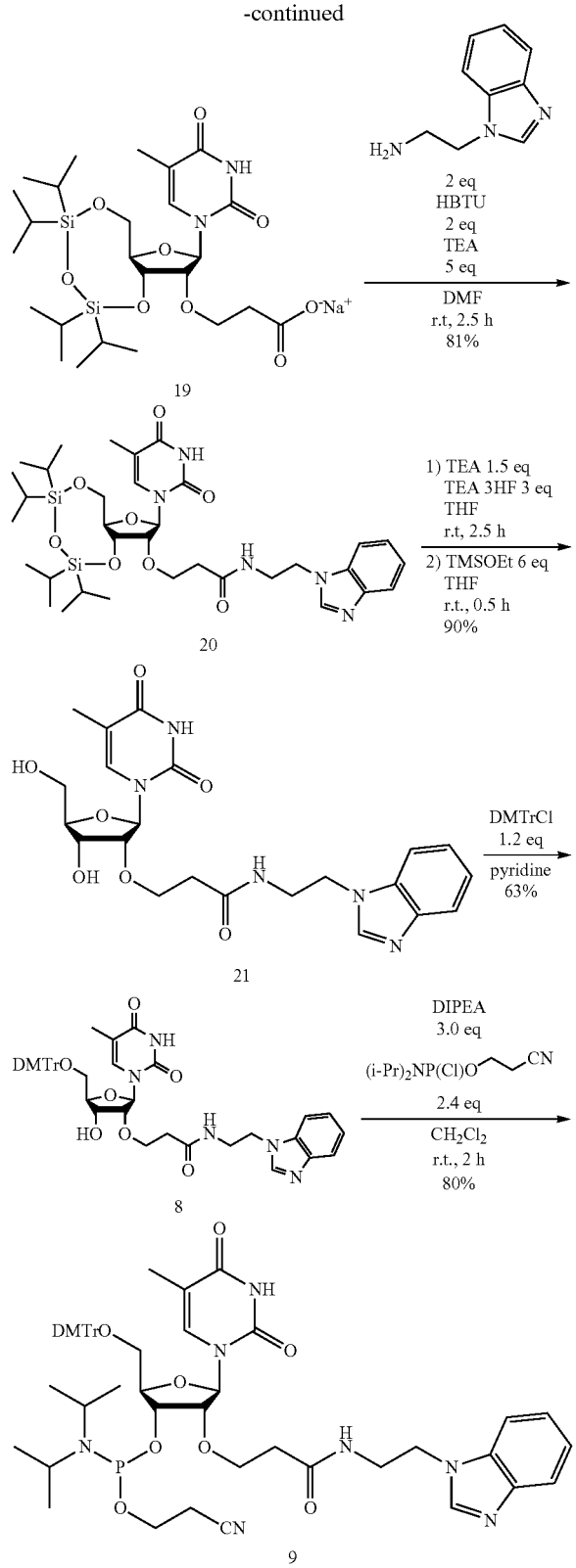

Example 4-2 Synthesis of Compound 18

Compound 17 (synthesized according to the method described in the Journal of Organic Chemistry, Vol. 54, p. 2321 (1989)) was dissolved in pyridine, concentrated under reduced pressure, dissolved in toluene, concentrated under reduced pressure, dissolved in dichloromethane and finally concentrated under reduced pressure. After repeating this procedure three times each, the resulting product was dissolved in a mixed solvent of tert-butyl alcohol and dichloromethane (20 ml, tert-butyl alcohol:dichloromethane=3/1 (volume ratio)). Cesium carbonate (650 mg, 2.0 mmol) and allyl acrylate (4.8 ml, 40 mmol) were added to that solution followed by stirring for 5 hours at room temperature. Following completion of the reaction, the solvent was distilled off under reduced pressure. Ethyl acetate was added to the resulting residue and washed with water. The organic layer was dried with anhydrous sodium sulfate and the solvent was distilled off under reduced pressure. The resulting residue was purified by silica gel column chromatography (developing solvent:hexane-ethyl acetate) to obtain Compound 18 (1.1 g, yield: 75%).

$^1$H NMR (CDCl$_3$, 500 MHz): δ 7.93 (dd, 2H), 7.71 (d, 1H), 7.68-7.62 (m, 1H), 7.50 (dd, 2H), 5.86 (ddt, 1H), 5.72 (s, 1H), 5.26 (dq, 1H), 5.17 (dq, 1H), 4.59-4.49 (m, 2H), 4.26 (d, 1H), 4.22 (dd, 1H), 4.11 (dd, 1H), 4.05 (t, 2H), 3.98 (dd, 1H), 3.90 (d, 1H), 2.67-2.54 (m, 2H), 1.95 (d, 3H), 1.14-0.96 (m, 28H).

Example 4-3 Synthesis of Compound 19

Compound 18 (684 mg, 1.1 mmol) was dissolved in anhydrous tetrahydrofuran (11 ml). Tetrakis(triphenylphosphine) palladium (0) (141 mg, 0.12 mmol) and morpholine (0.96 ml, 11 mmol) were added to that solution followed by stirring for 30 minutes at room temperature. Following completion of the reaction, the solvent was distilled off under reduced pressure. The resulting residue was purified by silica gel column chromatography (developing solvent: hexane-ethyl acetate) followed by passing through Dowex HCR-S strongly acidic ion exchange region (Na type) to convert to a sodium salt and obtain Compound 19 (450 mg, yield: 69%).

1H NMR (CDCl$_3$, 500 MHz): δ 10.74 (s, 1H), 7.64 (s, 1H), 5.71 (s, 1H), 4.30-4.18 (m, 3H), 4.12 (dd, 1H), 4.02 (dt, 1H), 3.97 (dd, 1H), 3.94 (d, 1H), 2.74-2.64 (m, 1H), 2.60-2.50 (m, 1H), 1.91 (s, 3H), 1.18-0.92 (m, 28H).

Example 4-4 Synthesis of Compound 20

Compound 19 (190 mg, 0.26 mmol) was dissolved in N,N-dimethylformamide (2.6 ml). O-benzotriazolyl-N,N,N', N'-tetramethyluronium hexafluorophosphate (HBTU, 187 mg, 0.52 mmol) and 1-(2-aminoethyl)benzimidazole (83 mg, 0.52 mmol) were added to that solution followed by stirring for 2.5 hours at room temperature. Following completion of the reaction, a mixed solvent of ethyl acetate and hexane (ethyl acetate/hexane=1/1 (volume ratio)) was added and washed with water. The organic layer was dried with anhydrous sodium sulfate and the solvent was distilled off under reduced pressure. The resulting residue was purified by silica gel column chromatography (developing solvent:hexane-ethyl acetate) to obtain Compound 20 (150 mg, yield: 81%).

MS (ESI): [M−H]$^−$ 714.3453.

$^1$H NMR (CDCl$_3$, 500 MHz): δ 9.62 (s, 1H), 7.94 (s, 1H), 7.79-7.70 (m, 1H), 7.48 (d, 1H), 7.45-7.41 (m, 1H), 7.29-7.20 (m, 2H), 5.34 (s, 1H), 4.40 (ddd, 1H), 4.33 (dt, 1H), 4.23-4.14 (m, 2H), 4.09 (dd, 1H), 3.91-3.73 (m, 4H), 3.65 (d, 1H), 3.57 (ddt, 1H), 2.55 (ddd, 1H), 2.48 (ddd, 1H), 1.86 (d, 3H), 1.11-0.86 (m, 28H).

Example 4-5 Synthesis of Compound 21

Compound 20 (555 mg, 0.78 mmol) was dissolved in anhydrous tetrahydrofuran (7.8 ml). Triethylamine (161 μl, 1.2 mmol) and triethylamine trihydrofluoride (370 μl, 2.3 mmol) were added to that solution followed by stirring for 2.5 hours at room temperature. Following the reaction, trimethylethoxysilane (723 μl, 4.7 mmol) were added to the reaction mixture followed by stirring for 30 minutes, filtering and drying the resulting solid under reduced pressure to obtain Compound 21 (330 mg, yield: 90%).

MS (ESI): [M−H]⁻ 472.1831.

$^1$H NMR (DMSO-$d_6$, 500 MHz) δ 11.34 (s, 1H), 8.16-8.09 (m, 2H), 7.78 (d, 1H), 7.64 (d, 1H), 7.58 (d, 1H), 7.26 (t, 1H), 7.19 (t, 1H), 5.83 (d, 1H), 5.21-5.16 (m, 2H), 4.29 (t, 2H), 4.17 (q, 1H), 3.93 (t, 1H), 3.84 (q, 1H), 3.74-3.52 (m, 4H), 3.48-3.38 (m, 2H), 2.35-2.24 (m, 2H), 1.76 (d, 3H).

Example 4-6 Synthesis of Compound 8

Compound 20 (310 mg, 0.65 mmol) was dissolved in pyridine and concentrated under reduced pressure, and after carrying out this procedure three times, the concentrated product was dissolved in pyridine (6.5 ml). 4,4'-dimethoxytrityl chloride (266 mg, 0.79 mmol) was added to that solution followed by stirring for 1 hour at room temperature. Following completion of the reaction, the solvent was distilled off under reduced pressure. Dichloromethane was added to the resulting residue followed by washing with aqueous sodium bicarbonate solution. The organic layer was dried with anhydrous sodium sulfate and the solvent was distilled off under reduced pressure. The resulting residue was purified by silica gel column chromatography (developing solvent:dichloromethane-methanol) to obtain Compound 8 (320 mg, yield: 63%).

MS (ESI): [M−H]⁻ 774.3140.

$^1$H NMR (CDCl$_3$, 500 MHz): δ 9.56 (s, 1H), 7.80 (s, 1H), 7.61-7.58 (m, 1H), 7.51 (d, 1H), 7.43-7.12 (m, 11H), 6.89-6.77 (m, 4H), 5.99 (d, 1H), 4.46 (t, 1H), 4.37-4.29 (m, 2H), 4.15-4.10 (m, 1H), 4.07-3.96 (m, 2H), 3.86 (dt, 1H), 3.83-3.73 (m, 7H), 3.59-3.46 (m, 2H), 3.39 (dd, 1H), 2.62-2.53 (m, 1H), 2.50-2.42 (m, 1H), 1.35 (s, 3H).

Example 4-7 Synthesis of Compound 9

A reaction was carried out using the same method as that described in Example 4-1 with the exception of using Compound 8 (320 mg, 0.41 mmol) instead of Compound 1 to obtain Compound 9 (325 mg, yield: 80%).

Example 5 Artificial Oligonucleotide Synthesis and Purification

Artificial oligonucleotides (Compounds 10 to 16, SEQ ID NO: 1 to 7, shown in the following Table 1) containing nucleoside structures derived from Compounds 3, 5, 7 and 9 obtained in Examples 1 to 4 were synthesized at the 1.0 μmol scale using the nS-8II automated nucleic acid synthesizer (manufactured by GeneDesign)).

The amidite units (Compounds 3, 5, 7 and 9) were used after dissolving in acetonitrile. Furthermore, in Table 1, the nucleotide structures derived from Compounds 3, 5, 7 and 9 are indicated as $X_1$, $X_2$, $X_3$ and $X_4$ in that order. In addition, in Table 1, "M" refers to a 2'-O-methyl nucleoside, upper case letters indicate deoxyribonucleotides, "A" indicates a phosphorothioate bond, "5" means that the nucleotide base is 5-methylcytosine.

Coupling time between the amidite unit (Compounds 3, 5, 7 and 9) and the hydroxyl group of the 5'-end was made to be 5 minutes. After treating oligonucleotide analogues, in which the 5'-end was protected with a DMTr group and which were supported on a solid phase, with saturated aqueous ammonia, the analogues were subjected to crude purification using Sep-Pak (Waters). These were then purified by reversed-phase HPLC (Shimadzu LC-6AD, Shimadzu SPD-M20A, preparatory column: Waters XBridge™ Prep C18 5 μm (10 mm×250 mm))

When the purity of the synthesized artificial oligonucleotides (Compounds 10 to 12) was confirmed by ion exchange chromatography, purities were determined to be 97% (Compound 10), 96% (Compound 11), 96% (Compound 12), 94% (Compound 14), 97% (Compound 15) and 96% (Compound 16). The purity of Compound 13 was determined to be 99% as confirmed by HPLC.

(Ion Exchange Chromatography Analysis Conditions)
Column: DNAPac PA-100 (Dionex, 4×250 mm)
Column temperature: 50° C.
Eluent: 25 mM sodium phosphate buffer (pH 6.0)/1 M sodium chloride-25 mM sodium phosphate buffer (pH 6.0) =100/0→(45 minutes)→40/60 Flow rate: 1.0 mL/min
(HPLC Analysis Conditions)
Eluent: Aqueous solution containing 0.1 M hexafluoroisopropyl alcohol and 8 mM triethylamine/methanol=95/5 (1 minute)→(14 minutes)→75/25 (3.5 minutes)
Flow rate: 1.0 mL/min
Column: Waters XBridge™ C18 2.5 μm, 4.6 mm×75 mm
Column temperature: 60° C.
Detection: UV (260 nm)

Molecular weights of the synthesized artificial oligonucleotides (Compounds 10 to 16) were determined by MALDI-TOF-MASS. The results are shown in Table 1.

TABLE 1

|  | Sequence | Molecular weight measured value (M-H-) | Remarks |
|---|---|---|---|
| Compound 10 | 5'-TTTTTTTTTTTTTTX$_1$X$_1$X$_1$X$_1$-3' | 6489.17 | SEQ ID NO: 1 |
| Compound 11 | 5'-TTTTTTTTTTTTTTX$_2$X$_2$X$_2$X$_2$-3' | 6353.59 | SEQ ID NO: 2 |
| Compound 12 | 5'-TTTTTTTTTTTTTTX$_3$X$_3$X$_3$X$_3$-3' | 6521.85 | SEQ ID NO: 3 |
| Compound 13 | 5'-TTTTTTTTTTTTTTX$_4$X$_4$X$_4$X$_4$-3' | 6643.93 | SEQ ID NO: 4 |

TABLE 1-continued

| | Sequence | Molecular weight measured value (M-H-) | Remarks |
|---|---|---|---|
| Compound 14 | 5'-5(M)^X$_1$^G(M)^5(M)^X$_1$^A^G^5^5^T^5^T^G^G^A^X$_1$^X$_1$^X$_1$^G(M)^A(M)-3' | 7857.66 | SEQ ID NO: 5 |
| Compound 15 | 5'-5(M)^X$_2$^G(M)^5(M)^X$_2$^A^G^5^5^T^5^T^G^G^A^X$_2$^X$_2$^X$_2$^G(M)^A(M)-3' | 7418.11 | SEQ ID NO: 6 |
| Compound 16 | 5'-5(M)^X$_3$^G(M)^5(M)^X$_3$^A^G^5^5^T^5^T^G^G^A^X$_3$^X$_3$^X$_3$^G(M)^A(M)-3' | 7628.09 | SEQ ID NO: 7 |

Reference Example 1 Synthesis of MOE Oligonucleotide

MCE Oligonucleotide and 2'-O-Methyl Oligonucleotide

An artificial oligonucleotide containing an MOE nucleoside structure represented by the following formula ($Q_1$) (Compound C1), artificial oligonucleotides containing an MCE nucleoside structure represented by formula ($Q_2$) (Compounds C2 and C3), and an artificial oligonucleotide containing a 2'-O-methyl ribonucleoside structure (Compound C4) were synthesized in the same manner as Example 5. Molecular weights were determined by MALDI-TOF-MASS. The results are shown in Table 2. Furthermore, in Table 2, the nucleotide structure represented by formula ($Q_1$) is indicated as $Q_1$, and the nucleotide structure represented by formula ($Q_2$) is indicated as $Q_2$. In addition, in Table 2, "(M)" refers to a 2'-O-methyl ribonucleoside, upper case letters refers to a deoxyribonucleotide, "^" indicates a phosphorothioate bond, and "5" means that the nucleotide base is 5-methylcytosine.

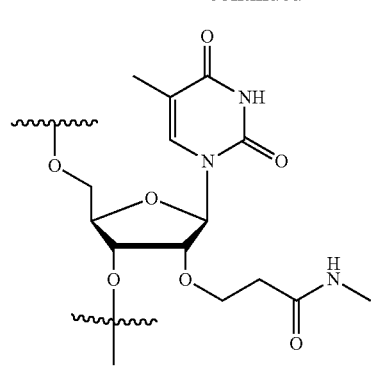

(Q$_2$)

TABLE 2

| | Sequence | Molecular weight measured value (M-H-) | Remarks |
|---|---|---|---|
| Compound C1 | 5'-TTTTTTTTTTTTTTQ$_1$Q$_1$Q$_1$Q$_1$-3' | 6013.33 | SEQ ID NO: 8 |
| Compound C2 | 5'-TTTTTTTTTTTTTTQ$_2$Q$_2$Q$_2$Q$_2$-3' | 6125.69 | SEQ ID NO: 9 |
| Compound C3 | 5'-5(M)^Q$_2$^G(M)^5(M)^Q$_2$^A^G^5^5 T^5^T^G^G^A^Q$_2$^Q$_2$^Q$_2$^G(M)^A(M)-3' | 7132.84 | SEQ ID NO: 10 |
| Compound C4 | 5'-5(M)^T(M)^G(M)^5(M)^T(M)^A^G^5^5^T^5^T^G^G^A^T(M)^T(M)^T(M)^G(M)^A(M)-3' | 6777.62 | SEQ ID NO: 11 |

Example 6 Evaluation of Nuclease Resistance of Artificial Oligonucleotides

A study was made of the resistance of the artificial oligonucleotides of Compound 10 (PyECE), Compound 11 (DMAECE) and Compound 12 (MorECE) synthesized in Example 5, along with the artificial oligonucleotide Compound C1 (MOE) and Compound C2 (MCE) synthesized in Reference Example 1, to exonuclease that degrades oligonucleotides from the 3'-side.

After holding a buffer solution (80 µL) containing 750 pmol of artificial oligonucleotide for 5 minutes at 37° C., the buffer solution was mixed with a buffer solution (20 µL) containing 0.2 µg of phosphodiesterase I (Worthington Biochemical Corp.). The residual amount of artificial oligonucleotide was measured over time by reversed-phase HPLC. Furthermore, the residual amount of artificial oligonucleotide was measured after immediately transferring the sample to an oil bath at 90° C. and holding therein for 5 minutes to deactivate the enzyme.

The composition (final concentrations) of the buffer used consisted of 50 mM Tris-HCl (tris(hydroxymethyl)ami-

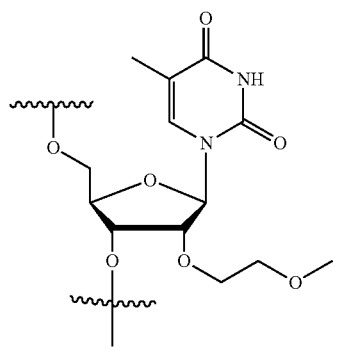

($Q_1$)

nomethane hydrochloride, pH 8.0) and 10 mM MgCl$_2$, and the buffer was adequately degassed prior to measurement. HPLC quantification conditions were as shown below.

(HPLC Analysis Conditions)

Eluent: Aqueous solution containing 0.1 M hexafluoroisopropyl alcohol and 8 mM triethylamine/methanol=95/5 (1 minute)→(14 minutes)→75/25 (3.5 minutes)

Flow rate: 1.0 mL/min

Column: Waters XBridge™ C18 2.5 µm, 4.6 mm×75 mm

Column temperature: 60° C.

Detection: UV (260 nm)

The results are shown in FIG. 1. In FIG. 1, "Full Length Oligo (%)" indicates the residual percentage of undegraded oligonucleotide (19 mer) at the time of measurement to undegraded oligonucleotide (19 mer) at time 0. In addition, "Time (min)" indicates the time at which the measurement was made (units: minutes).

As a result, all of the MOE oligonucleotide (MOE) degraded after 60 minutes. The residual percentage of the MCE oligonucleotide was 10% even after 120 minutes and the residual percentage thereof was 2% after 180 minutes. On the other hand, the residual percentages of Compound 10 (PyECE), Compound 11 (DMAECE) and Compound 12 (MorECE) after 120 minutes were 38%, 29% and 50%, respectively, while the residual percentages after 180 minutes were 24%, 14% and 36%, respectively. Thus, Compound 10 (PyECE), Compound 11 (DMAECE) and Compound 12 (MorECE) were determined to have enzyme resistance that far exceeds that of artificial oligonucleotides (MOE and MCE) prepared from known artificial nucleotides.

Example 7 Evaluation of Nuclease Resistance of Artificial Oligonucleotides

A study was made of the resistance of the artificial oligonucleotide of Compound 13 (BimECE) synthesized in Example 5 and the artificial oligonucleotide of Compound C2 (MCE) synthesized in Reference Example 1 to exonuclease that degrades oligonucleotides from the 3'-side. Treatment and analysis conditions were the same as in Example 6.

Figure 2:
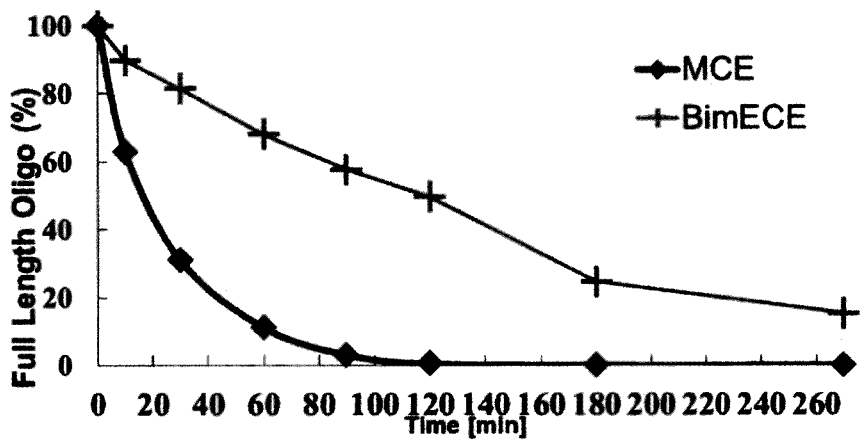
FIG. 2 is a graph indicating exonuclease resistance of artificial oligonucleotides according to the present embodiment.

The results are shown in FIG. 2. In FIG. 2, "Full Length Oligo (%)" indicates the residual percentage of undegraded oligonucleotide (19 mer) at the time of measurement to undegraded oligonucleotide (19 mer) at time 0. In addition, "Time (min)" indicates the time at which the measurement was made (units: minutes).

As a result, the MCE oligonucleotide (MCE) was nearly completely degraded after 120 minutes. On the other hand, the residual percentage of Compound 13 (BimECE) after 120 minutes was 50% and the residual percentage thereof after 180 minutes was 24%. Thus, the BimECE oligonucleotide (BimECE) was determined to have enzyme resistance that far exceeds that of an artificial oligonucleotide (MCE) prepared from a known artificial nucleotide.

Example 8 Measurement of Melting Temperature (Tm)

Antisense hybridization ability was investigated by measuring Tm value after carrying out annealing treatment of the artificial oligonucleotides of Compounds 14 to 16 synthesized in Example 5 (antisense strands) and an RNA sense strand (3'-UCAAAUCCAGAGGCUAGCAG-5').

An artificial oligonucleotide containing an MCE nucleoside structure (Compound C3) and an artificial oligonucleotide containing a 2'-O-methyl ribonucleoside structure (Compound C4) were used as controls.

Each single strand of the synthesized oligonucleotides (sense strand and antisense strand) was dissolved with Milli-Q water (ultrapure water produced with the Milli-Q™ Ultrapure Water Purification System) and adjusted to a concentration of 2 µM. 380 µL of a solution having a final concentration of 1 µM was prepared by sampling and mixing 190 µL of the concentration-adjusted sense strand and antisense strand. Next, the Milli-Q water was distilled off under reduced pressure. This sample was dissolved in 190 µL of 10 mM sodium phosphate buffer (pH 7.0) containing 100 mM sodium chloride and 0.1 mM ethylenediamine tetraacetate to bring to a final concentration of 2 µM. Next, heating and cooling were carried out using a thermal cycler. First, after raising the temperature to 95° C., that temperature was maintained for 5 minutes followed by lowering the temperature to 30° C. at the rate of 1° C. per minute to carry out annealing.

Next, the annealed sample was diluted with water for injection until absorbance at 260 nm reached a value of 2. 150 µL of this sample having an absorbance of 2, 30 µL of 10×PBS(−) and 120 µL of water for injection were mixed to prepare 300 µL of measurement solution.

After installing a cell containing the sample in a spectrophotometer (Shimadzu, Pharma Spec UV-1700), the sample solution was heated to 90° C. and measurement was started after further holding at 90° C. for 10 minutes. The temperature was then lowered to 5° C. in 0.5° C. increments and UV absorbance at 260 nm was measured at 1° C. intervals. Subsequently, the temperature was conversely raised from 5° C. to 90° C. in 0.5° C. increments and UV absorbance at 260 nm was measured at 0.5° C. intervals. Measurements were carried out three times. Table 3 indicates the average value and standard deviation of Tm values when measuring while raising the temperature. Furthermore, covered cells were used to prevent changes in concentration due to temperature increases, and dehumidified air was passed through the cell to prevent condensation of moisture.

TABLE 3

| | Tm average ± standard deviation (° C.) |
|---|---|
| Compound 14 | 68.7 ± 0.4 |
| Compound 15 | 69.4 ± 0.5 |
| Compound 16 | 68.9 ± 0.2 |
| Compound C3 | 69.9 ± 0.4 |
| Compound C4 | 69.1 ± 0.4 |

As is clear from Table 3, affinity of artificial oligonucleotides of the present embodiment to single-stranded RNA was determined to be comparable to that of artificial oligonucleotides prepared from known artificial nucleotides (MEC nucleotide and 2'-O-methyl ribonucleoside).

Example 9 Artificial Oligonucleotide Synthesis and Purification

An artificial oligonucleotide (Compound 17, SEQ ID NO: 12, shown in the following Table 4) containing a nucleoside structure derived from Compound 9 obtained in Example 4 was synthesized at the 1.0 μmol scale using the nS-8II automated nucleic acid synthesizer (manufactured by GeneDesign)).

The amidite unit (Compound 9) was used after dissolving in acetonitrile. Furthermore, the sequence notations used in Table 4 are the same as those of Table 1.

Coupling time between the amidite unit (Compound 9) and the hydroxyl group of the 5'-end was made to be 15 minutes. After treating an oligonucleotide analogue, in which the 5'-end was protected with a DMTr group and which was supported on a solid phase, with saturated aqueous ammonia, the analogue was subjected to crude purification with Glen-Pak (Glen Research). This was then purified by reversed-phase HPLC (Shimadzu LC-6AD, Shimadzu SPD-M20A, preparatory column: Waters XBridge™ Prep C18 5 μm (10 mm×250 mm)).

When the purity of the synthesized artificial oligonucleotide (Compound 17) was confirmed by HPLC, purity was determined to be 99%.

(HPLC Analysis Conditions)

Eluent: Aqueous solution containing 0.1 M hexafluoroisopropyl alcohol and 8 mM triethylamine/methanol=95/5 (1 minute)→(14 minutes)→75/25 (3.5 minutes)

Flow rate: 1.0 mL/min

Column: Waters XBridge™ C18 2.5 μm, 4.6 mm×75 mm

Column temperature: 60° C.

Detection: UV (260 nm)

The molecular weight of the synthesized artificial oligonucleotide (Compound 17) was determined by MALDI-TOF-MASS. The results are shown in Table 4.

TABLE 4

| Sequence | | Molecular weight measured value (M − H⁻) | Remarks |
|---|---|---|---|
| Compound 17 | 5'-A(M)^C(M)^A(M)^A(M)^A(M)^C(M)^A(M)^C(M)^C(M)^A(M)^X₄^X₄^G(M)^X₄^C(M)^A(M)^C(M)^A(M)^C(M)^X₄^C(M)^C(M)^A(M) -3' | 8755.43 | SEQ ID NO: 12 |

Reference Example 2 Synthesis of MCE Oligonucleotide

An artificial oligonucleotide containing an MCE nucleoside structure represented by formula ($Q_2$) (Compound C5) was synthesized in the same manner as Example 9. Molecular weight was determined by MALDI-TOF-MASS. The results are shown in Table 5. Furthermore, in Table 5, the nucleotide structure represented by formula ($Q_2$) is indicated $Q_2$. In addition, the sequence notations used in Table 5 are the same as those of Table 2.

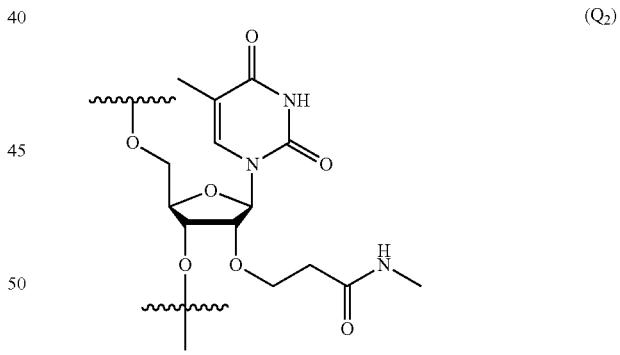

($Q_2$)

TABLE 5

| Sequence | | Molecular weight measured value (M − H⁻) | Remarks |
|---|---|---|---|
| Compound C5 | 5' -A(M)^C(M)^A(M)^A(M)^A(M)^C(M)^A(M)^C(M)^C(M)^A(M)^Q₂^Q₂^G(M)^Q₂^C(M)^A(M)^C(M)^A(M)^C(M)^Q₂^C(M)^C(M)^A(M) -3' | 8235.01 | SEQ ID NO: 13 |

Example 10 Evaluation of Antisense Activity

Figure 3:
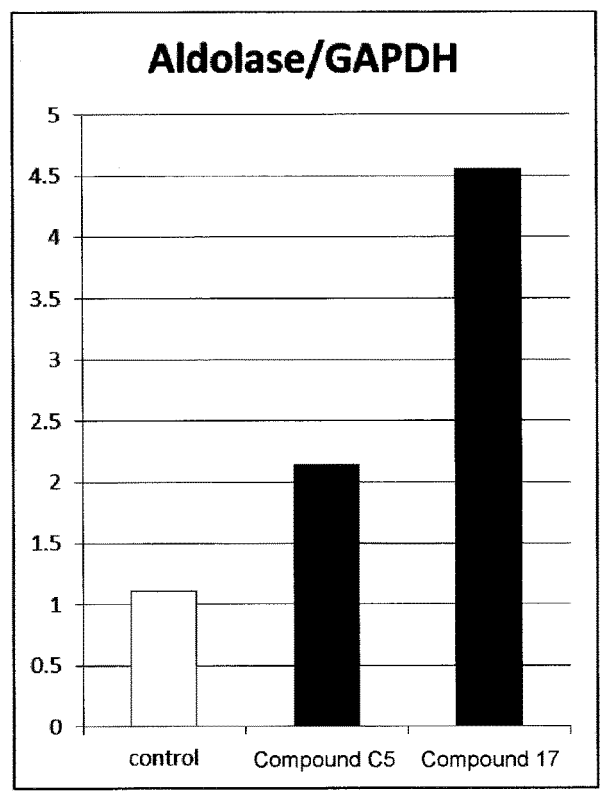
FIG. 3 is a graph indicating the effect of artificial oligonucleotides according to the present embodiment on the expression level of aldolase A in human hepatoma-derived cells.
Figure 4:
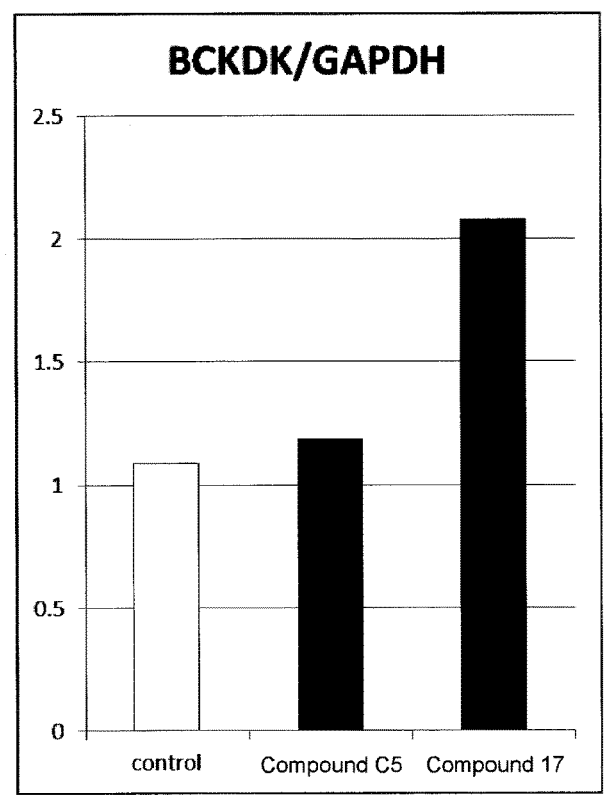
FIG. 4 is a graph indicating the effect of artificial oligonucleotides according to the present embodiment on the expression level of BCKDK in human hepatoma-derived cells.

Human hepatoma cell line HuH-7 cells were disseminated at 3000 cells/well in a 96-well plate and cultured for 24 hours at 37° C. in the presence of 5% $CO_2$. Compound 17 and Compound C5 were added to each well to a final concentration of 0.1 nM using Lipofectamine® RNAiMax (Thermo Fisher Scientific) (transfection). The medium was replaced after 4 hours and the cells were recovered after 7 days followed by extracting total RNA from the cells using the RNeasy Mini Kit (Qiagen)

cDNA was obtained from the total RNA using PrimeScript RT Master Mix (Takara Bio). Real-time PCR was then carried out with the 7500 Real-Time PCR System (Applied Biosystems) using the resulting cDNA and TaqMan® Gene Expression ID (Applied Biosystems) to determine the amounts of aldolase A mRNA and branched chain ketoacid dehydrogenase kinase (BCKDK) mRNA as target genes of miRNA-122. During real-time PCR, the amount of glyceraldehyde-3-phosphate dehydrogenase (GAPDH) mRNA as a housekeeping gene was simultaneously assayed. The amount of Aldolase A mRNA relative to the amount of GAPDH mRNA was evaluated as the expression level of Aldolase A, the amount of BCKDK mRNA relative to the amount of GAPDH mRNA was evaluated as the expression level of BCKDK. Cells that did not undergo the transfection procedure were used as a control. The results are shown in FIGS. 3 and 4. At this time, high expression levels of aldolase A and BCKDK indicate a high antisense effect.

Furthermore, primers used consisted of the TaqMan Gene Expression Assay (Applied Biosystems) and the Assay ID were as indicated below.

Human aldolase A assay: Hs00605108_g1
Human BCKDK assay: Hs00195380_m1
Human GAPDH assay: Hs99999905_m1

As is clear from FIGS. 3 and 4, Compound 17 was confirmed to demonstrate a higher antisense effect than Compound C5.

INDUSTRIAL APPLICABILITY

The artificial oligonucleotide prepared from the nucleoside analogue or nucleotide analogue of the present invention demonstrates extremely superior nuclease resistance. Thus, since the oligonucleotide is thought to demonstrate extremely favorable sustained action in the body, the nucleoside analogue or nucleotide analogue of the present invention is extremely useful as a material for synthesizing nucleic acid pharmaceuticals such as antisense oligonucleotides.

---

The invention claimed is:

1. A compound represented by the following formula (I):

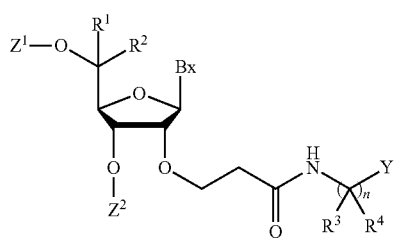

wherein,

Bx represents a purin-9-yl group, 2-oxo-pyrimidin-1-yl group or 2-thioxo-pyrmidin-1-yl group in which the purin-9-yl group, 2-oxo-pyrimidin-1-yl group and 2-thioxo-pyrimidin-1-yl group are, independently of each other, unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group, $Z^1$ and $Z^2$, independently of each other, represent a hydrogen atom, hydroxyl group-protecting group or phosphorous-containing group, $R^1$, $R^2$, $R^3$ and $R^4$, independently of each other, represent a hydrogen atom, halogen atom, cyano group, C1-6 alkyl group or C2-6 alkenyl group in which the C1-6 alkyl group and C2-6 alkenyl group are unsubstituted or substituted with one or more substituents solely or differently selected from the group consisting of a halogen atom, C1-6 alkoxy group and cyano group, Y represents $NR^5R^6$, wherein $R^5$ and $R^6$, together with a nitrogen atom bound thereto, form a 3- to 11-membered nitrogen-containing non-aromatic heterocyclic group in which the 3- to 11-membered nitrogen-containing non-aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group, or C2-9 aromatic heterocyclic group in which the C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group, and n represents an integer of 1 to 3; wherein, when n is 2 or 3, two or three $R^3$ and $R^4$ may respectively be the same or different, or a salt thereof.

2. The compound according to claim 1, wherein Bx represents a 6-aminopurin-9-yl group, 2-amino-6-hydroxypurin-9-yl group, 2-oxo-4-amino-1,2-dihydropyrimidin-1-yl group, 2-oxo-4-amino-5-methyl-1,2-dihydropyrimidin-1-yl group, 2-oxo-4-hydroxy-1,2-dihydropyrimidin-1-yl group or 2-oxo-4-hydroxy-5-methyl-1,2-dihydropyrimidin-1-yl group, or the salt thereof.

3. The compound according to claim 1, wherein $R^1$, $R^2$, $R^3$ and $R^4$ represent hydrogen atoms, or the salt thereof.

4. The compound according to claim 1, wherein Y represents $NR^5R^6$, and $R^5$ and $R^6$, together with a nitrogen atom bound thereto, form morpholine, or the salt thereof.

5. The compound according to claim 1, wherein Y represents a pyridyl group, imidazolyl group or benzimidazolyl group, or the salt thereof.

6. The compound according to claim 1, wherein n is 2, or the salt thereof.

7. The compound according to claim 1, wherein $Z^1$ represents a hydrogen atom or hydroxyl group-protecting group, or salt thereof.

8. The compound according to claim 1, wherein $Z^2$ represents a hydrogen atom or phosphorous-containing group, or the salt thereof.

9. The compound according to claim 1, wherein $Z^2$ represents a hydroxyl group-protecting group, or the salt thereof.

10. An artificial oligonucleotide containing one or more nucleoside structures represented by the following formula (II):

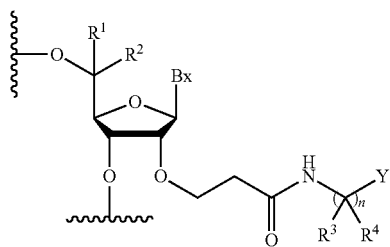

wherein,

Bx represents a purin-9-yl group, 2-oxo-pyrimidin-1-yl group or 2-thioxo-pyrmidin-1-yl group in which the purin-9-yl group, 2-oxo-pyrimidin-1-yl group and 2-thioxo-pyrimidin-1-yl group are, independently of each other, unsubstituted or substituted with one or more substituents solely or differently selected from the group consisting of a halogen atom, C1-6 alkyl group, amino group, amino group substituted with an amino group-protecting group, hydroxyl group, hydroxyl group substituted with a hydroxyl group-protecting group, sulfanyl group and sulfanyl group substituted with a sulfanyl group-protecting group, $R^1$, $R^2$, $R^3$ and $R^4$, independently of each other, represent a hydrogen atom, halogen atom, cyano group, C1-6 alkyl group or C2-6 alkenyl group in which the C1-6 alkyl group and C2-6 alkenyl group are unsubstituted or substituted with one or more substituents solely or differently selected from the group consisting of a halogen atom, C1-6 alkoxy group and cyano group, Y represents $NR^5R^6$, wherein $R^5$ and $R^6$, together with a nitrogen atom bound thereto, form a 3- to 11-membered nitrogen-containing non-aromatic heterocyclic group in which the 3- to 11-membered nitrogen-containing non-aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group, or C2-9 aromatic heterocyclic group in which the C2-9 aromatic heterocyclic group is unsubstituted or substituted with one or more substituents solely or differently selected from the group consisting of a halogen atom, cyano group, nitro group, amino group, hydroxyl group, carboxy group, carbamoyl group, C1-6 alkyl group, C2-6 alkenyl group, C1-6 alkoxy group, C2-6 alkenyloxy group, C1-6 alkoxycarbonyl group, C2-6 alkenyloxycarbonyl group, C1-6 alkylcarbonyl group, C1-6 haloalkyl group, C1-6 alkylamino group, C1-6 alkylaminocarbonyl group, C1-6 alkylcarbonyloxy group, C1-6 alkylcarbonylamino group and C1-6 alkoxycarbonylamino group, and n represents an integer of 1 to 3; wherein, when n is 2 or 3, two or three $R^3$ and $R^4$ may respectively be the same or different, or a pharmaceutically acceptable salt thereof.

11. The artificial oligonucleotide according to claim 10, wherein Bx represents a 6-aminopurin-9-yl group, 2-amino-6-hydroxypurin-9-yl group, 2-oxo-4-amino-1,2-dihydropyrimidin-1-yl group, 2-oxo-4-amino-5-methyl-1,2-dihydropyrimidin-1-yl group, 2-oxo-4-hydroxy-1,2-dihydropyrimidin-1-yl group or 2-oxo-4-hydroxy-5-methyl-1,2-dihydropyrimidin-1-yl group, or the pharmaceutically acceptable salt thereof.

12. The artificial oligonucleotide according to claim 10, wherein $R^1$, $R^2$, $R^3$ and $R^4$ represent hydrogen atoms, or the pharmaceutically acceptable salt thereof.

13. The artificial oligonucleotide according to claim 10, wherein Y represents $NR^5R^6$, and $R^5$ and $R^6$, together with a nitrogen atom bound thereto, form morpholine, or the pharmaceutically acceptable salt thereof.

14. The artificial oligonucleotide according to claim 10, wherein Y represents a pyridyl group, imidazolyl group or benzimidazolyl group, or the pharmaceutically acceptable salt thereof.

15. The artificial oligonucleotide according to claim 10, wherein n is 2, or the pharmaceutically acceptable salt thereof.

16. The compound according to claim 1, wherein Y represents $NR^5R^6$, and $R^5$ and $R^6$, together with a nitrogen atom bound thereto, form a 4- to 8-membered nitrogen-containing non-aromatic heterocyclic group.

17. The compound according to claim 1, wherein Y represents a C2-9 aromatic heterocyclic group.

18. The artificial oligonucleotide according to claim 10, wherein Y represents $NR^5R^6$, and $R^5$ and $R^6$, together with a nitrogen atom bound thereto, form a 4- to 8-membered nitrogen-containing non-aromatic heterocyclic group.

19. The artificial oligonucleotide according to claim 10, wherein Y represents a C2-9 aromatic heterocyclic group.

* * * * *